(12) United States Patent
Schaffer et al.

(10) Patent No.: US 8,501,905 B2
(45) Date of Patent: Aug. 6, 2013

(54) SYNTHETIC CELL PLATFORMS AND METHODS OF USE THEREOF

(75) Inventors: David V. Schaffer, Pleasant Hill, CA (US); Kevin Edward Healy, Moraga, CA (US); Lauren Little, Oakland, CA (US); Patrick Sean Daugherty, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 494 days.

(21) Appl. No.: 12/532,098

(22) PCT Filed: Mar. 21, 2008

(86) PCT No.: PCT/US2008/003811
§ 371 (c)(1),
(2), (4) Date: Mar. 18, 2010

(87) PCT Pub. No.: WO2008/118392
PCT Pub. Date: Oct. 2, 2008

(65) Prior Publication Data
US 2010/0189760 A1    Jul. 29, 2010

Related U.S. Application Data

(60) Provisional application No. 60/919,640, filed on Mar. 22, 2007.

(51) Int. Cl.
*C07K 2/00* (2006.01)
*C07K 5/00* (2006.01)

(52) U.S. Cl.
USPC .......................................... 530/300; 530/327

(58) Field of Classification Search
None
See application file for complete search history.

(56) References Cited

U.S. PATENT DOCUMENTS

| 5,863,650 | A | 1/1999 | Healy et al. |
| 7,157,275 | B2 | 1/2007 | Guarino et al. |
| 2004/0001892 | A1 | 1/2004 | Healy et al. |
| 2007/0026518 | A1* | 2/2007 | Healy et al. ............ 435/325 |
| 2007/0099247 | A1 | 5/2007 | Daugherty et al. |

FOREIGN PATENT DOCUMENTS

WO   WO 2006054262   5/2006

* cited by examiner

*Primary Examiner* — Albert Navarro
(74) *Attorney, Agent, or Firm* — Paula A. Borden; Bozicevic, Field & Francis LLP

(57) ABSTRACT

The present invention provides synthetic cell platforms. The synthetic cell platforms can be used for culturing cells in vitro. The synthetic cell platforms can also be implanted together with bound cells into an individual. The present invention provides methods of using the platforms to provide cells or progeny of such cells for use in various applications, including clinical applications; and methods of use of the platforms to introduce cells into an individual.

7 Claims, 14 Drawing Sheets a)
1. WWCDMRGDSRCSG
2. YMCMSRGDATCDV
3. QCCQLRGDAVCNC
4. WVCNKLGVYACEY
5. LECTERGDFNCFV
6. ESCWYQIMYKCAN

SEQUENCE LISTING

```
<160> NUMBER OF SEQ ID NOS: 103

<210> SEQ ID NO 1
<211> LENGTH: 11
<212> TYPE: PRT
<213> ORGANISM: Artificial Sequence
<220> FEATURE:
<223> OTHER INFORMATION: Consensus sequence

<400> SEQUENCE: 1

Arg Lys Arg Asp Arg Leu Gly Thr Leu Gly Ile
 1               5                  10

<210> SEQ ID NO 2
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 2

Cys Gly Gly Asn Gly Glu Pro Arg Gly Asp Thr Tyr Arg Ala Tyr
 1               5                  10                  15

<210> SEQ ID NO 3
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 3

Cys Glu Pro Arg Gly Asp Thr Tyr Arg Ala Tyr Gly
 1               5                  10

<210> SEQ ID NO 4
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 4

Val Ser Trp Phe Ser Arg His Arg Tyr Ser Pro Phe Ala Val Ser
 1               5                  10                  15

<210> SEQ ID NO 5
<211> LENGTH: 11
<212> TYPE: PRT
<213> ORGANISM: Artificial Sequence
<220> FEATURE:
```

```
<223> OTHER INFORMATION: Synthetic Peptide

<400> SEQUENCE: 5

Cys Thr Arg Lys Lys His Asp Asn Ala Gln Cys
1               5                   10

<210> SEQ ID NO 6
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 6

Lys Gln Asn Cys Leu Ser Ser Arg Ala Ser Arg Gly Cys Val Arg Asn
1               5                   10                  15

Leu Arg Leu Ser Arg
            20

<210> SEQ ID NO 7
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 7

Asp His Lys Phe Gly Leu Val Met Leu Asn Lys Tyr Ala Tyr Ala Gly
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 8

Leu Glu Asp Ala Met Gly Trp Ala Leu Ser Trp Gly His Ile Trp
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 9

Ser Asp Trp Ser Val Leu Leu Ser Cys Glu Arg Trp Tyr Cys Ile
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 10

Arg Arg Glu Leu Val Arg Met Thr Asp Trp Val Trp Val Ser Gly
1               5                   10                  15

<210> SEQ ID NO 11
<211> LENGTH: 15
<212> TYPE: PRT
<213> ORGANISM: Artificial Sequence
```

-continued

```
<220> FEATURE:
<223> OTHER INFORMATION: Synthetic Peptide

<400> SEQUENCE: 11

Gly Phe Val Leu Val Trp Ser Tyr Thr Cys Arg Cys Trp Gly Lys
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 12

Glu Ser Gly Leu Lys Val Met Cys Met Lys Tyr Tyr Cys Met Ala
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 13

Asp Leu Cys Thr Tyr Gly His Leu Trp Leu Gly Asn Gly Arg Pro
1               5                   10                  15

<210> SEQ ID NO 14
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 14

Trp Tyr Cys Phe Arg Glu Asn Lys Tyr Val Cys Val Met
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 15

Glu Ser Cys Trp Tyr Gln Ile Met Tyr Lys Cys Ala Asn
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 16

Trp Phe Cys Leu Leu Gly Arg Ser Ala Tyr Cys Val Arg
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Synthetic Peptide
```

<400> SEQUENCE: 17

Tyr Met Cys Met Ser Arg Gly Asp Ala Thr Cys Asp Val
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 18

Ile Trp Cys Gly Ser Arg Phe Gly Cys Trp Cys Lys Pro
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 19

Gly Glu Cys Phe Tyr Tyr Val Met Asn Thr Cys Val Trp
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 20

Leu Glu Cys Thr Glu Arg Gly Asp Phe Asn Cys Phe Val
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 21

Trp Leu Cys Leu Asp Lys Asn Cys Met Ala Cys Val Trp
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 22

Lys Leu Cys Cys Phe Asp Lys Gly Tyr Tyr Cys Met Arg
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 23

```
Leu Cys Cys Glu Ser Tyr Ile Cys Ala Leu Cys His Tyr
 1               5                  10
```

<210> SEQ ID NO 24
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 24

```
Phe Trp Cys Ile Arg Gly Glu Tyr Trp Val Cys Asp Arg
 1               5                  10
```

<210> SEQ ID NO 25
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 25

```
Leu Asn Cys Ala Met Tyr Asn Ala Cys Ile Trp
 1               5                  10
```

<210> SEQ ID NO 26
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 26

```
Gln Cys Cys Gln Leu Arg Gly Asp Ala Val Cys Asn Cys
 1               5                  10
```

<210> SEQ ID NO 27
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 27

```
Trp Leu Cys Lys Gly Ser Asn Lys Tyr Met Cys Glu Trp
 1               5                  10
```

<210> SEQ ID NO 28
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 28

```
Trp Val Cys Asn Lys Leu Gly Val Tyr Ala Cys Glu Tyr
 1               5                  10
```

<210> SEQ ID NO 29
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 29

```
Trp Val Cys Ile Trp Glu Arg Phe Lys Ser Cys Asn Glu
```

<210> SEQ ID NO 30
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 30

Trp Asn Cys Ile Lys Gly Ser Ser Trp Ala Cys Val Trp
 1               5                  10

<210> SEQ ID NO 31
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 31

Trp Met Cys Ser Gly Val Gln Pro Asn Ala Cys Val Trp
 1               5                  10

<210> SEQ ID NO 32
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 32

Trp Trp Cys Asp Met Arg Gly Asp Ser Arg Cys Ser Gly
 1               5                  10

<210> SEQ ID NO 33
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 33

Ser Leu Cys Ala Ala Tyr Asn Arg Trp Ala Cys Ile Trp
 1               5                  10

<210> SEQ ID NO 34
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 34

Trp Ser Cys Pro Lys Val Asn Gln Tyr Ala Cys Phe Trp
 1               5                  10

<210> SEQ ID NO 35
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 35

Gly Gly Cys Arg Trp Tyr Ala Lys Trp Val Cys Val Trp
 1               5                  10

```
<210> SEQ ID NO 36
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 36

Trp Asp Cys Gly Lys Lys Asn Ala Trp Met Cys Ile Trp
1               5                   10

<210> SEQ ID NO 37
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 37

Trp Thr Trp Glu Ser Ala Phe Ala Gly Arg Trp Glu Val Gly Asp
1               5                   10                  15

<210> SEQ ID NO 38
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 38

Ser Lys Cys Trp Gly Trp Thr Pro Tyr Tyr Cys Val Ala
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 39

Trp Arg Cys Leu Gly Asp Gly Tyr His Ala Cys Val Arg
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 40

Leu Glu Cys Pro Gly Glu Ser Lys Tyr Tyr Cys Ile Tyr
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 41

Trp Val Cys Leu Trp Arg His Arg Gly Asp Cys Ser Ile
1               5                   10

<210> SEQ ID NO 42
```

```
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 42

Ser Thr Cys Ser Trp Val Ser Ser Tyr Val Cys Ile Met
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 43

Trp Val Cys Asn Asp Leu Ile His His Phe Cys Val Trp
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 44

Gln Gly Cys Ala Phe Val Thr Tyr Trp Ala Cys Ile Phe
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 45

Trp Glu Cys Ala Glu Glu Ser Lys Phe Trp Cys Val Phe
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 46

Trp Trp Cys Lys Lys Pro Glu Tyr Trp Tyr Cys Ile Trp
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 47

Trp Gln Cys Gly Arg Phe Trp Cys Ile His Cys Leu Trp
1               5                   10

<210> SEQ ID NO 48
<211> LENGTH: 13
<212> TYPE: PRT
```

```
<213> ORGANISM: Artificial Sequence
<220> FEATURE:
<223> OTHER INFORMATION: Synthetic Peptide

<400> SEQUENCE: 48

Arg Leu Cys Cys Trp Lys Thr Gln Tyr Phe Cys Glu Ile
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 49

Met Tyr Cys Glu Arg Asp Ser Lys Tyr Trp Cys Ile His
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 50

Val Trp Cys Gly Met Phe Gly Lys Arg Arg Cys Val Thr
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 51

Leu Val Cys Asn Arg Gln Asn Pro Trp Val Cys Tyr Ile
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 52

Cys Gly Gly Glu Pro Arg Gly Asp Thr Tyr Arg Ala
1               5                   10

<210> SEQ ID NO 53
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 53

Cys Gly Pro Arg Gly Asp Thr Tyr
1               5

<210> SEQ ID NO 54
<211> LENGTH: 9
<212> TYPE: PRT
<213> ORGANISM: Artificial Sequence
<220> FEATURE:
```

<223> OTHER INFORMATION: Synthetic Peptide

<400> SEQUENCE: 54

Cys Gly Pro Arg Gly Asp Thr Tyr Gly
1               5

<210> SEQ ID NO 55
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 55

Trp Val Cys Asn Lys Leu Gly Val Tyr Ala Cys Glu Tyr
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 56

Cys Gly Gly Phe His Arg Arg Ile Lys Ala
1               5                   10

<210> SEQ ID NO 57
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 57

Cys Gly Gly Asp Gly Glu Ala Gly
1               5

<210> SEQ ID NO 58
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 58

Cys Gly Gly Asn Gly Glu Pro Arg Gly Glu Thr Tyr Arg Ala Tyr
1               5                   10                  15

<210> SEQ ID NO 59
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 59

Ile Lys Val Ala Val
1               5

<210> SEQ ID NO 60
<211> LENGTH: 16
<212> TYPE: PRT
<213> ORGANISM: Artificial Sequence
<220> FEATURE:
<223> OTHER INFORMATION: Synthetic Peptide

```
<400> SEQUENCE: 60

Asp His Lys Phe Gly Leu Val Met Leu Asn Lys Tyr Ala Tyr Ala Gly
 1               5                  10                  15

<210> SEQ ID NO 61
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 61

Gly Gly Cys Arg Trp Tyr Ala Lys Trp Val Cys Val Trp
 1               5                  10

<210> SEQ ID NO 62
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 62

Ser Lys Cys Trp Gly Trp Thr Pro Tyr Tyr Cys Val Ala
 1               5                  10

<210> SEQ ID NO 63
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 63

Val Trp Cys Gly Met Phe Gly Lys Arg Arg Cys Val Thr
 1               5                  10

<210> SEQ ID NO 64
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 64

Trp Asn Cys Ile Lys Gly Ser Ser Trp Ala Cys Val Trp
 1               5                  10

<210> SEQ ID NO 65
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 65

Trp Tyr Cys Phe Arg Glu Asn Lys Tyr Val Cys Val Met
 1               5                  10

<210> SEQ ID NO 66
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 66
```

```
Trp Ser Cys Pro Lys Val Asn Gln Tyr Ala Cys Phe Trp
1               5                   10
```

<210> SEQ ID NO 67
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 67

```
Trp Val Cys Leu Trp Arg His Arg Gly Asp Cys Ser Ile
1               5                   10
```

<210> SEQ ID NO 68
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 68

```
Ser Leu Cys Ala Ala Tyr Asn Arg Trp Ala Cys Ile Trp
1               5                   10
```

<210> SEQ ID NO 69
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 69

```
Trp Arg Cys Leu Gly Asp Gly Tyr His Ala Cys Val Arg
1               5                   10
```

<210> SEQ ID NO 70
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 70

```
Leu Glu Cys Pro Gly Glu Ser Lys Tyr Tyr Cys Ile Tyr
1               5                   10
```

<210> SEQ ID NO 71
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 71

```
Trp Glu Cys Ala Glu Glu Ser Lys Phe Trp Cys Val Phe
1               5                   10
```

<210> SEQ ID NO 72
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 72

```
Trp Phe Cys Leu Leu Gly Arg Ser Ala Tyr Cys Val Arg
1               5                   10
```

```
<210> SEQ ID NO 73
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 73

Gln Gly Cys Ala Phe Val Thr Tyr Trp Ala Cys Ile Phe
 1               5                  10

<210> SEQ ID NO 74
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 74

Lys Leu Cys Cys Phe Asp Lys Gly Tyr Tyr Cys Met Arg
 1               5                  10

<210> SEQ ID NO 75
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 75

Trp Trp Cys Lys Lys Pro Glu Tyr Trp Tyr Cys Ile Trp
 1               5                  10

<210> SEQ ID NO 76
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 76

Leu Val Cys Asn Arg Gln Asn Pro Trp Val Cys Tyr Ile
 1               5                  10

<210> SEQ ID NO 77
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 77

Trp Val Cys Asn Asp Leu Ile His His Phe Cys Val Trp
 1               5                  10

<210> SEQ ID NO 78
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 78

Arg Leu Cys Cys Trp Lys Thr Gln Tyr Phe Cys Glu Ile
 1               5                  10
```

```
<210> SEQ ID NO 79
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 79

Met Tyr Cys Glu Arg Asp Ser Lys Tyr Trp Cys Ile His
 1               5                   10

<210> SEQ ID NO 80
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 80

Arg Arg Glu Leu Val Arg Met Thr Asp Trp Val Trp Val Ser Gly
 1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 81

Leu Glu Asp Ala Met Gly Trp Ala Leu Ser Trp Gly His Ile Trp
 1               5                   10                  15

<210> SEQ ID NO 82
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 82

Trp Leu Cys Leu Asp Lys Asn Cys Met Ala Cys Val Trp
 1               5                   10

<210> SEQ ID NO 83
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 83

Trp Leu Cys Lys Gly Ser Asn Lys Tyr Met Cys Glu Trp
 1               5                   10

<210> SEQ ID NO 84
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 84

Trp Asp Cys Gly Lys Lys Asn Ala Trp Met Cys Ile Trp
 1               5                   10

<210> SEQ ID NO 85
<211> LENGTH: 13
```

```
<212> TYPE: PRT
<213> ORGANISM: Artificial Sequence
<220> FEATURE:
<223> OTHER INFORMATION: Synthetic Peptide

<400> SEQUENCE: 85

Trp Val Cys Ile Trp Glu Arg Phe Lys Ser Cys Asn Glu
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 86

Ile Trp Cys Gly Ser Arg Phe Gly Cys Trp Cys Lys Pro
1               5                   10

<210> SEQ ID NO 87
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 87

Gly Phe Val Leu Val Trp Ser Tyr Thr Cys Arg Cys Trp Gly Lys
1               5                   10                  15

<210> SEQ ID NO 88
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 88

Ser Thr Cys Ser Trp Val Ser Ser Tyr Val Cys Ile Met
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 89

Phe Trp Cys Ile Arg Gly Glu Tyr Trp Val Cys Asp Arg
1               5                   10

<210> SEQ ID NO 90
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 90

Ser Asp Trp Ser Val Leu Leu Ser Cys Glu Arg Trp Tyr Cys Ile
1               5                   10                  15

<210> SEQ ID NO 91
<211> LENGTH: 15
<212> TYPE: PRT
<213> ORGANISM: Artificial Sequence
```

```
<220> FEATURE:
<223> OTHER INFORMATION: Synthetic Peptide

<400> SEQUENCE: 91

Glu Ser Gly Leu Lys Val Met Cys Met Lys Tyr Tyr Cys Met Ala
1               5                   10                  15

<210> SEQ ID NO 92
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 92

Tyr Met Cys Met Ser Arg Gly Asp Ala Thr Cys Asp Val
1               5                   10

<210> SEQ ID NO 93
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 93

Gly Glu Cys Phe Tyr Tyr Val Met Asn Thr Cys Val Trp
1               5                   10

<210> SEQ ID NO 94
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 94

Trp Trp Cys Asp Met Arg Gly Asp Ser Arg Cys Ser Gly
1               5                   10

<210> SEQ ID NO 95
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 95

Trp Thr Trp Glu Ser Ala Phe Ala Gly Arg Trp Glu Val Gly Asp
1               5                   10                  15

<210> SEQ ID NO 96
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 96

Glu Ser Cys Trp Tyr Gln Ile Met Tyr Lys Cys Ala Asn
1               5                   10

<210> SEQ ID NO 97
<211> LENGTH: 11
<212> TYPE: PRT
<213> ORGANISM: Artificial Sequence
<220> FEATURE:
<223> OTHER INFORMATION: Synthetic Peptide
```

```
<400> SEQUENCE: 97

Leu Asn Cys Ala Met Tyr Asn Ala Cys Ile Trp
1               5                   10

<210> SEQ ID NO 98
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 98

Gln Cys Cys Gln Leu Arg Gly Asp Ala Val Cys Asn Cys
1               5                   10

<210> SEQ ID NO 99
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 99

Trp Gln Cys Gly Arg Phe Trp Cys Ile His Cys Leu Trp
1               5                   10

<210> SEQ ID NO 100
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 100

Leu Glu Cys Thr Glu Arg Gly Asp Phe Asn Cys Phe Val
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 101

Trp Met Cys Ser Gly Val Gln Pro Asn Ala Cys Val Trp
1               5                   10

<210> SEQ ID NO 102
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 102

Leu Cys Cys Glu Ser Tyr Ile Cys Ala Leu Cys His Tyr
1               5                   10

<210> SEQ ID NO 103
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 103
```

```
Asp Leu Cys Thr Tyr Gly His Leu Trp Leu Gly Asn Gly Arg Pro
1               5                   10                  15
```

SYNTHETIC CELL PLATFORMS AND METHODS OF USE THEREOF

CROSS-REFERENCE

This application claims the benefit of U.S. Provisional Patent Application No. 60/919,640, filed Mar. 22, 2007, which application is incorporated herein by reference in its entirety.

BACKGROUND

Human embryonic stem cells (hESCs) have potential as sources of cells for the treatment for disease and injury (e.g. tissue engineering and reconstruction, diabetes, Parkinson's Disease, leukemia, congestive heart failure, etc.). Features that are important for successful integration of hESC into such therapies include: expansion of hESCs without differentiation (i.e., self-renewal), differentiation of hESCs into a specific cell type or collection of cell types, and functional integration of hESCs or their progeny into existing tissue. Current ex vivo culture systems for hESCs include mouse and human feeder cell layers, media conditioned by feeder cells, or serum-free conditions with complex extracellular matrix proteins. Such systems pose a number of problems, including poorly characterized environmental signals, the transmission of pathogens to hESCs, the transfer of (and "contamination" with) immunogenic epitopes to hESCs leading to rejection after engraftment, poor availability of large-scale supplies of reproducibly high quality purified proteins, and limitations on the ability to scale-up to a clinical process for the treatment of thousands or even millions of patients. In addition, the grafting of hESCs or their differentiated progeny in vivo for tissue repair often suffers from poor cell viability. Therefore, improved platforms are needed for enhancing the survival of implanted cells.

There is a need in the art for improved culture systems and methods for generating stem cells, e.g., hESCs, and/or progeny thereof for clinical use.

Literature

U.S. Pat. No. 7,157,275; U.S. Patent Publication No. 2007/0026518; U.S. Pat. No. 5,863,650; U.S. Patent Publication No. 2004/0001892; and U.S. Patent Publication No. 2007/0099247.

SUMMARY OF THE INVENTION

The present invention provides synthetic cell platforms. The synthetic cell platforms can be used for culturing cells in vitro. The synthetic cell platforms can also be implanted together with bound cells into an individual. The present invention provides methods of using the platforms to provide cells or progeny of such cells for use in various applications, including clinical applications; and methods of use of the platforms to introduce cells into an individual.

DEFINITIONS

Figure 1:
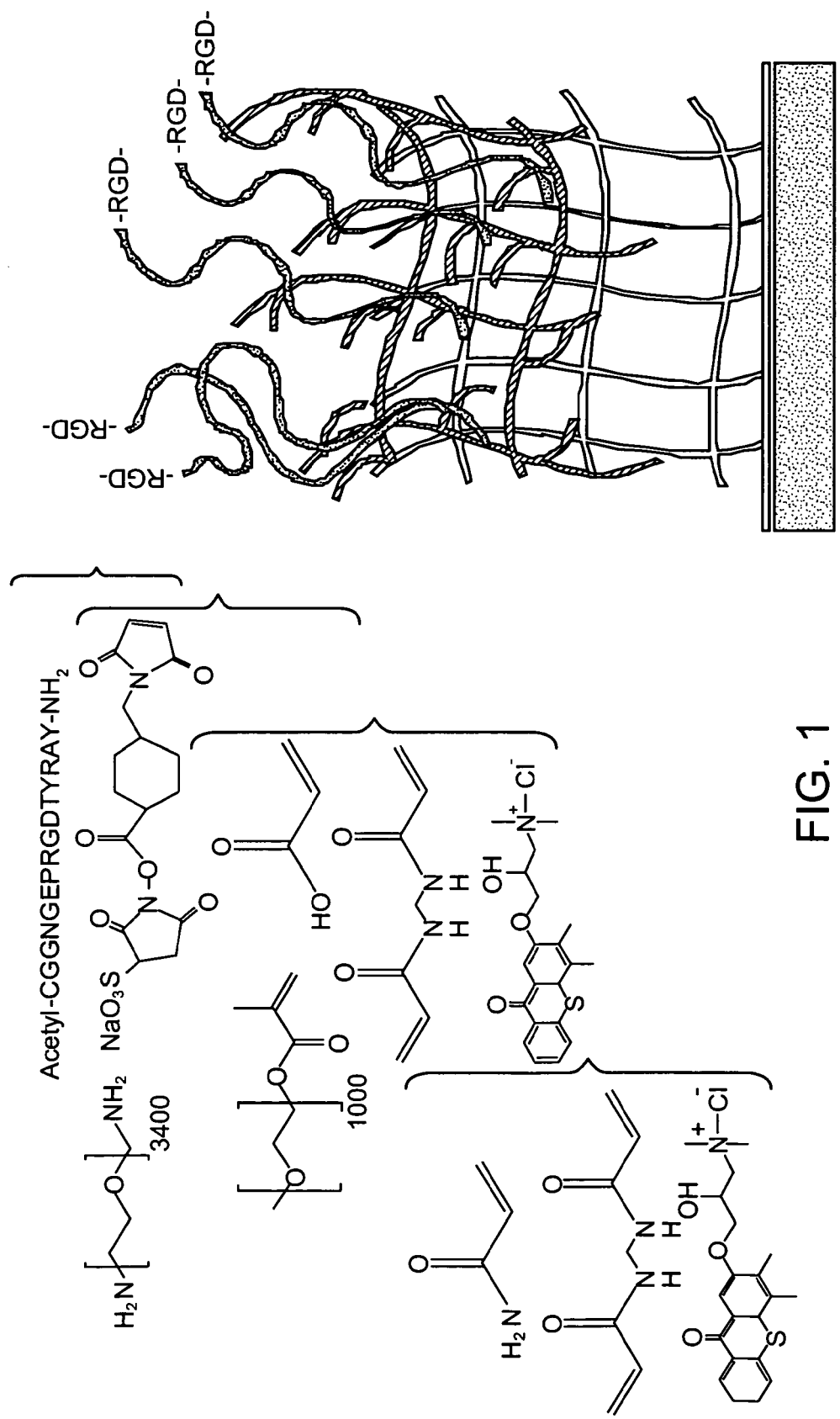
FIG. 1 is a schematic depiction of a biomimetic interpenetrating polymer network.

As used herein, the term "stem cell" refers to an undifferentiated cell that can be induced to proliferate. The stem cell is capable of self-maintenance or self-renewal, meaning that with each cell division, one daughter cell will also be a stem cell. Stem cells can be obtained from embryonic, post-natal, juvenile, or adult tissue. Stem cells can be pluripotent or multipotent. The term "progenitor cell," as used herein, refers to an undifferentiated cell derived from a stem cell, and is not itself a stem cell. Some progenitor cells can produce progeny that are capable of differentiating into more than one cell type.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," "recipient," and "patient," used interchangeably herein, refer to a mammal, including, but not limited to, rodents (e.g., rats, mice), non-human primates, humans, canines, felines, ungulates (e.g., equines, bovines, ovines, porcines, caprines), etc.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a stem cell" includes a plurality of such stem cells and reference to "the cell culture platform" includes reference to one or more cell culture platforms and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present invention provides synthetic cell platforms. The synthetic cell platforms can be used for culturing cells in vitro. The synthetic cell platforms can also be implanted together with bound cells into an individual. The present invention provides methods of using the platforms to provide cells or progeny of such cells for use in various applications, including clinical applications; and methods of use of the platforms to introduce cells into an individual.

Methods of Identifying Peptide Ligands

The present invention provides methods of identifying peptide ligands of mammalian cell surface molecule (e.g., a cell surface macromolecule such as a protein, a glycoprotein, etc.). The methods generally involve contacting a mammalian cell in vitro with a population of bacteria comprising individual bacteria, each of which displays on its surface a different heterologous peptide, forming a mixed mammalian cell population comprising mammalian cells bound to one or more bacteria and unbound bacterial cells; and separating the bound from the unbound bacterial cells. Binding of a mammalian cell to a bacterium indicates that the bacterium displays on its cell surface a peptide that binds to a mammalian cell surface molecule. The heterologous peptide displayed by the bacterium is considered a candidate cell surface-binding peptide for use in a subject synthetic cell platform. Methods of generating a peptide display library include, e.g., a method as described in U.S. Patent Publication No. 2007/0099247, which is incorporated herein by reference.

A peptide-displaying bacterium displays a peptide at a density of from about $10^3$ to about $10^5$ peptides per bacterial cell, e.g., at a density of from about $10^3$ to about $5 \times 10^3$, from about $5 \times 10^3$ to about $10^4$, from about $10^4$ to about $5 \times 10^4$, or from about $5 \times 10^4$ to about $10^5$, or more, peptide molecules per cell. Each bacterium in a peptide-displaying bacterial population (or "library") displays a different peptide. A peptide-displaying bacterial library can display two, three, four, five, six, seven, eight, nine, ten, from 10 to 25, from 25 to 50, from 50 to 100, from $10^2$ to $10^4$, from $10^4$ to $10^6$, from $10^6$ to $10^8$, from $10^8$ to $10^9$, or from $10^9$ to about $10^{10}$, or more, different peptides, each present on the surface of different bacteria in the library population.

A peptide displayed by a peptide-displaying bacterium is "heterologous," e.g., the peptide is one that is not normally synthesized by the bacterium. Each heterologous peptide can have a length of from about 5 amino acids to about 50 amino acids, e.g., from about 5 amino acids to about 10 amino acids, from about 10 amino acids to about 15 amino acids, from about 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, from about 40 amino acids to about 45 amino acids, or from about 45 amino acids to about 50 amino acids.

In some embodiments, the heterologous peptide is displayed as a fusion protein of a bacterial protein, e.g., a fusion protein comprising a bacterial protein (e.g., a protein that the bacterium normally synthesizes) fused in-frame to a heterologous peptide. The heterologous peptide can be fused to the amino terminus of the bacterial protein, to the carboxyl-terminus of the bacterial protein, or at an internal site of the bacterial protein. The fusion protein is synthesized by the bacterium such that the heterologous peptide is displayed on the surface of the bacterium, e.g., a surface that is accessible for binding by a mammalian cell when the bacterium and the mammalian cell are brought into contact in vitro.

In some embodiments, the heterologous peptide is displayed as a fusion protein with an outer membrane protein (OMP) of a bacterium. In some embodiments, the heterologous peptide is a C-terminal or N-terminal fusion protein with a circularly permuted variant of outer membrane protein X (CPX). CPX is described in, e.g., Rice et al. (2006) *Protein Science* 15:825-836. See also, U.S. Patent Publication No. 2007/0099247.

In some embodiments, the peptide-displaying bacteria are genetically modified to produce a fluorescent protein, e.g., the peptide-displaying bacteria are genetically modified by introduction into the bacteria of a nucleic acid comprising a nucleotide sequence encoding a fluorescent protein, where the nucleic acid is, e.g., an expression vector that provides for expression of the nucleotide sequence in the bacteria. Suitable fluorescent proteins include, but are not limited to, a green fluorescent protein (GFP; Chalfie, et al., *Science* 263 (5148):802-805 (Feb. 11, 1994); an enhanced GFP (EGFP), e.g., Genbank Accession Number U55762); a blue fluorescent protein (BFP; Stauber, R. H. *Biotechniques* 24(3):462-471 (1998); Heim, R. and Tsien, R. Y. *Curr. Biol.* 6:178-182 (1996)); a yellow fluorescent protein (YFP); an enhanced yellow fluorescent protein (EYFP); luciferase (Ichiki, et al., *J. Immunol.* 150(12):5408-5417 (1993)); a fluorescent protein as described in, e.g., WO 92/15673, WO 95/07463, WO 98/14605, WO 98/26277, WO 99/49019, U.S. Pat. Nos. 5,292,658, 5,418,155, 5,683,888, 5,741,668, 5,777,079, 5,804,387, 5,874,304, 5,876,995, or 5,925,558); a cyan fluorescent protein (CFP); a GFP from a species such as *Renilla reniformis, Renilla mulleri*, or *Ptilosarcus guernyi*, as described in, e.g., WO 99/49019 and Peelle et al. (2001) *J. Protein Chem.* 20:507-519; and any of a variety of fluorescent and colored proteins from Anthozoan species, as described in, e.g., Matz et al. (1999) *Nature Biotechnol.* 17:969-973; U.S. Patent Publication No. 2002/0197676, or U.S. Patent Publication No. 2005/0032085; and the like.

Where the bacteria are genetically modified to produce a fluorescent protein, bound mammalian cells (e.g., mammalian cells to which are bound one or more peptide-displaying bacteria) are separated from unbound mammalian cells using a fluorescence-activated cell sorting (FACS) method.

In some embodiments, the mammalian cells are genetically modified to produce a detectable signal upon binding of a peptide-displaying bacterium that displays a peptide that activates a cell signaling pathway. Signaling pathways include, but are not limited to, phosphoinositide-3 kinase (PI 3-kinase), mitogen-activated protein kinase (MAPK), phospholipase C (PLC), protein kinase C (PKC), protein kinase A (PICA), protein kinase G (PKG), Sonic hedgehog (Shh), Wnt, Notch, Jak/STAT, and calcium/calmodulin dependent kinase (Cam kinase). The assay used to detect activation of a cell signaling pathway can depend, e.g., on the mode of transmission of the signal and/or the nature of the components of the signaling pathway. For example, in some embodiments, detecting activation of a signaling pathway involves detecting activity of a kinase involved in the signaling pathway. In other embodiments, detecting activation of a signaling pathway involves detecting a change in intracellular calcium concentration ($[Ca^{2+}]_i$). In other embodiments, detecting activation of a signaling pathway involves detecting relocalization of one or more molecules in the cell interior (e.g., relocalization of a protein from the cytoplasm to the nucleus, and the like). In some embodiments, a fluorescence resonance energy transfer (FRET)-based assay is used.

As one non-limiting example, to detect activation of a signaling pathway, the activity of a kinase can be detected, e.g., phosphorylation of Akt by PDK1; and the like. In some embodiments, a FRET-based assay is used. In some embodiments, a mammalian cell is genetically modified with a nucleic acid comprising a nucleotide sequence that encodes, in order from amino terminus to carboxyl terminus, a first member of a FRET pair (e.g., a FRET donor), a phosphoamino acid binding domain, an amino acid sequence that is specifically recognized and phosphorylated by the kinase, and a second member of a FRET pair (e.g., a FRET acceptor). Various fluorescent proteins can serve as FRET pairs. For example, CFP has an excitation maximum at 433 nm and an emission maximum at 476 nm, and can be used as a donor fluorophore in combination with a YFP as an acceptor (emission maximum at 527 nm). As another example, a BFP can be used as a donor fluorophore in combination with a GFP as the acceptor, or a CFP can be used as the donor fluorophore in combination with a YFP as the acceptor.

In some embodiments, the first member of the FRET pair is a CFP; and the second member of the FRET pair is a YFP. In some embodiments, the phosphoamino acid binding domain is an FHA2 phosphothreonine-binding domain. In some embodiments, the amino acid sequence that is specifically recognized and phosphorylated by the kinase is a consensus PKB phosphorylation sequence RKRDRLGTLGI (SEQ ID NO:1), where the underlined T is the phospho-acceptor residue. In some embodiments, the first and/or the second member of the FRET pair is a mutant CFP or a mutant YFP, e.g., a CFP or a YFP with a A206K mutation that renders the protein monomeric. See, e.g., Jones et al. (1991) *Proc. Natl. Acad. Sci. U.S.A.* 88:4171-4175; and Kunkel et al. (2005) *J. Biol. Chem.* 280:5581-5587. In some embodiments, the fluorescent protein is a mutant as described in Nguyen and Daugherty (2005) *Nat. Biotechnol.* 23:355-360.

FRET is phenomenon known in the art wherein excitation energy of one fluorescent dye is transferred to another without emission of a photon. A FRET pair consists of a donor fluorophore and an acceptor fluorophore (where the acceptor fluorophore may be a quencher molecule). The fluorescence emission spectrum of the donor and the fluorescence absorption spectrum of the acceptor must overlap, and the two molecules must be in close proximity. The distance between donor and acceptor at which 50% of donors are deactivated (transfer energy to the acceptor) is defined by the Förster radius, which is typically 10-100 angstroms. Changes in the fluorescence emission spectrum comprising FRET pairs can be detected, indicating changes in the number of that are in close proximity (i.e., within 100 angstroms of each other). This will typically result from the binding or dissociation of two molecules, one of which is labeled with a FRET donor and the other of which is labeled with a FRET acceptor, wherein such binding brings the FRET pair in close proximity. Suitable FRET acceptors and donors (e.g., first and second members of a FRET pair) include the above-mentioned fluorescent proteins, e.g, cyan fluorescent protein (CFP), yellow fluorescent protein, red fluorescent protein, green fluorescent protein, and the like.

Binding of such molecules will result in an increased fluorescence emission of the acceptor and/or quenching of the fluorescence emission of the donor. As an example, for detecting activation of Akt, a donor cyan fluorescent protein (CFP) and acceptor yellow fluorescent protein (YFP) with an intervening Akt substrate peptide yields FRET signal changes with Akt signaling and phosphorylation. This system can be adapted to provide for analysis of activation of any of a number of kinases. In some embodiments, a CFP mutant (e.g., A206K mutant) and a YFP mutant (e.g., A206K mutant) are used, which mutants are described in, e.g., Nguyen and Daugherty (2005) *Nat. Biotechnol.* 23:355-360; and Shaner et al. (2005) *Nat. Methods* 2:905-909. Akt is also known in the art as protein kinase B (PKB). A PKB sensor (also referred to as a B kinase activity reporter, or BKAR) is depicted schematically in FIG. 9. An expression construct comprises a nucleotide sequence encoding CFP, the FHA2 domain of Rad53p, a consensus PKB phosphorylation sequence (e.g., RKRDRLGTLGI (SEQ ID NO:1), where the underlined T is the phospho-acceptor residue), and YFP. See, e.g., Kunkel et al. (2005) *J. Biol. Chem.* 280:5581-5587. In the presence of active PKB, BKAR undergoes a conformational change, such that no signal is produced.

Peptides

The present invention provides peptides, e.g., isolated peptides or synthetic peptides, identified by a subject screening method, as described above. The peptides are useful for generating synthetic cell platforms, as described below. Peptides include, but are not limited to, integrin-binding peptides; peptides that bind a non-integrin adhesion receptor on the surface of a mammalian cell; peptides that activate a signaling pathway in a mammalian cell; and the like.

A subject peptide can have a length of from about 5 amino acids to about 50 amino acids, e.g., from about 5 amino acids to about 10 amino acids, from about 10 amino acids to about 15 amino acids, from about 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, from about 40 amino acids to about 45 amino acids, or from about 45 amino acids to about 50 amino acids.

Exemplary peptides are show in Tables 1-4, below, and also in Table 5 in Example 5.

TABLE 1

| Peptide Sequence | Receptor Target | Protein Source |
|---|---|---|
| CGGNGEPRGDTYRAY (bsp-RGD(15)) (SEQ ID NO: 2) | $\alpha_v\beta_3$ | Bone sialoprotein, vitronectin |
| C*EPRGDTYRAYG* [c-bsp-RGD(12)] (SEQ ID NO: 3) | $\alpha_v\beta_3$ | Bone sialoprotein, vitronectin |
| VSWFSRHRYSPFAVS (SEQ ID NO: 4) | $\alpha_6\beta_1$ | Laminin-1 ($\alpha$) |
| C*TRKKHDNAQC* (SEQ ID NO: 5) | $\alpha_2\beta_1$ | Coll(I), Laminin-1 ($\alpha$) |
| KQNCLSSRASRGCVRNLRLSR (SEQ ID NO: 6) | $\alpha_3\beta_1$ | Laminin-1 ($\alpha$) |

TABLE 2

| Clone | Peptide Sequence | |
|---|---|---|
| 15-2 | DHKFGLVMLNKYAYAG | (SEQ ID NO: 7) |
| 15-6 | LEDAMGWALSWGHIW | (SEQ ID NO: 8) |
| 15-16 | SDWSVLLSCERWYCI | (SEQ ID NO: 9) |
| 15-32 | RRELVRMTDWVWVSG | (SEQ ID NO: 10) |
| 15-50 | GFVLVWSYTCRCWGK | (SEQ ID NO: 11) |
| 15-52 | ESGLKVMCMKYYCMA | (SEQ ID NO: 12) |
| 15-59 | DLCTYGHLWLGNGRP | (SEQ ID NO: 13) |

TABLE 3

| Clone | Peptide sequence | |
|---|---|---|
| 7C-1 | WYCFRENKYVCVM | (SEQ ID NO: 14) |
| 7C-2 | ESCWYQIMYKCAN | (SEQ ID NO: 15) |
| 7C-3 | WFCLLGRSAYCVR | (SEQ ID NO: 16) |
| 7C-4 | YMCMSRGDATCDV | (SEQ ID NO: 17) |
| 7C-5 | IWCGSRFGCWCKP | (SEQ ID NO: 18) |
| 7C-6 | GECFYYVMNTCVW | (SEQ ID NO: 19) |
| 7C-7 | LECTERGDFNCFV | (SEQ ID NO: 20) |
| 7C-8 | WLCLDKNCMACVW | (SEQ ID NO: 21) |
| 7C-9 | KLCCFDKGYYCMR | (SEQ ID NO: 22) |
| 7C-11 | LCCESYICALCHY | (SEQ ID NO: 23) |
| 7C-12 | FWCIRGEYWVCDR | (SEQ ID NO: 24) |
| 7C-14 | LNCAMYNACIW | (SEQ ID NO: 25) |
| 7C-15 | QCCQLRGDAVCNC | (SEQ ID NO: 26) |
| 7C-17 | WLCKGSNKYMCEW | (SEQ ID NO: 27) |
| 7C-19 | WVCNKLGVYACEY | (SEQ ID NO: 28) |
| 7C-20 | WVCIWERFKSCNE | (SEQ ID NO: 29) |
| 7C-21 | WNCIKGSSWACVW | (SEQ ID NO: 30) |
| 7C-22 | WMCSGVQPNACVW | (SEQ ID NO: 31) |
| 7C-24 | WWCDMRGDSRCSG | (SEQ ID NO: 32) |

TABLE 4

| Clone | Peptide Sequence | |
|---|---|---|
| Co-1 | SLCAAYNRWACIW | (SEQ ID NO: 33) |
| Co-2 | WSCPKVNQYACFW | (SEQ ID NO: 34) |
| Co-3 | GGCRWYAKWVCVW | (SEQ ID NO: 35) |
| Co-5 | WDCGKKNAWMCIW | (SEQ ID NO: 36) |
| Co-8 | WTWESAFAGRWEVGD | (SEQ ID NO: 37) |
| Co-9 | SKCWGWTPYYCVA | (SEQ ID NO: 38) |
| Co-10 | WRCLGDGYHACVR | (SEQ ID NO: 39) |
| Co-11 | LECPGESKYYCIY | (SEQ ID NO: 40) |
| Co-12 | WVCLWRHRGDCSI | (SEQ ID NO: 41) |
| Co-13 | STCSWVSSYVCIM | (SEQ ID NO: 42) |
| Co-15 | WVCNDLIHHFCVW | (SEQ ID NO: 43) |
| Co-16 | QGCAFVTYWACIF | (SEQ ID NO: 44) |
| Co-17 | WECAEESKFWCVF | (SEQ ID NO: 45) |
| Co-18 | WWCKKPEYWYCIW | (SEQ ID NO: 46) |
| Co-19 | WQCGRFWCIHCLW | (SEQ ID NO: 47) |
| Co-20 | RLCCWKTQYFCEI | (SEQ ID NO: 48) |
| Co-21 | MYCERDSKYWCIH | (SEQ ID NO: 49) |
| Co-22 | VWCGMFGKRRCVT | (SEQ ID NO: 50) |
| Co-23 | LVCNRQNPWVCYI | (SEQ ID NO: 51) |

Further exemplary peptides are shown in Table 5, in Example 5. In some embodiments, a subject peptide comprises an amino acid sequence as shown in Tables 1-5 (e.g., a subject peptide comprises an amino acid sequence as set forth in any one of SEQ ID NOs: 2-51, and 60-103). For example, any of the peptide sequences depicted in Tables 1-5 (e.g., SEQ ID NOs: 2-51, and 60-103) can include one or more additional amino acids on the amino- and/or carboxyl-terminus of the peptide. In some embodiments, the peptide includes a linker that provides for linkage to a matrix or synthetic substrate, as described in more detail below. Also included are peptides that include one or more amino acid substitutions compared to a peptide sequence depicted in Tables 1-5 (e.g., any one of SEQ ID NOs: 2-51, and 60-103). In some embodiments, a subject peptide comprises an amino acid sequence of any one of SEQ ID NOs: 7-103. In some embodiments, a subject peptide comprises an amino acid sequence of any one of SEQ ID NOs: 7-51 and 60-103.

In some embodiments, a peptide comprising one or more of the following sequences is specifically excluded: RGD, FHR-RIKA, PRRARV, REDV, DEGA, YIGSR, IKVAV, PHSRN, and KGD, and cyclic variants thereof. In some embodiments, one or more of the peptides shown in Table 1 (SEQ ID NOs: 2-6) are specifically excluded. In some embodiments, a peptide comprising one or more of SEQ ID NOs:52-59 is specifically excluded.

Peptides can be synthesized using standard methods for chemical synthesis of a peptide. Peptides can also be synthesized recombinantly, using standard methods.

In some embodiments, a subject peptide, when contacted with a stem cell, induces differentiation of the stem cell in vitro and/or in vivo. In other embodiments, a subject peptide, when contacted with a stem cell, promotes growth of the stem cell without inducing differentiation of the stem cell, in vitro and/or in vivo. In some embodiments, a subject peptide, when contacted with a stem cell, self-renewal of the stem cell in vitro and/or in vivo. In other embodiments, a subject peptide promotes growth (proliferation) of a differentiated cell in vitro and/or in vivo.

Synthetic Cell Platforms

The present invention provides a synthetic cell platform that comprises a synthetic substrate and a cell surface-binding peptide. In some embodiments, the cell surface-binding peptide is a peptide identified by a subject method. A subject synthetic cell culture platform is useful for culturing cells in vitro, where the synthetic cell culture platform promotes growth and/or differentiation of a cell in in vitro culture. A subject synthetic cell culture platform can also be implanted into an individual along with cultured cells. As such, in some embodiments, a subject synthetic cell culture platform is also an implantable cell matrix.

Suitable cell surface-binding peptides include any of the peptides depicted in Tables 1-5 (SEQ ID NOs:2-51, and 60-103), or variants thereof. In some embodiments, suitable cell surface-binding peptides include any of the peptides depicted in Tables 2-5 (SEQ ID NOs:7-51 and 60-103), or variants thereof, including cyclic variants. A cell surface-binding peptide can be covalently linked to the synthetic substrate. A subject synthetic cell platform can comprise a single type ("species") of cell-binding peptide, e.g., where peptides of a given type or species all have the same amino acid sequence; or can include two or more types of cell-binding peptides, e.g., can comprise peptides of two or more (e.g., two, three, four, five, or more) different amino acid sequences that target the same cell surface receptor or class of cell surface receptors, or that target different cell surface receptors. For example, a subject cell platform can comprise a single peptide species having an amino acid sequence, where the peptide species binds a single type of cell. As another example, a subject cell platform can comprise a first peptide species having a first amino acid sequence, where the first peptide species binds a cell of a first cell type; a second peptide species having a second amino acid sequence that is different from the first amino acid sequence, where the second peptide species binds a cell of a second cell type that is different from the first cell type; etc.

A cell-binding peptide is bound to a synthetic substrate at a density of from about 0.01 pmol/cm$^2$ to about 100 pmol/cm$^2$, e.g., from about 0.01 pmol/cm$^2$ to about 0.1 pmol/cm$^2$, from about 0.1 pmol/cm$^2$ to about 1 pmol/cm$^2$, from about 1 pmol/cm$^2$ to about 10 pmol/cm$^2$, from about 10 pmol/cm$^2$ to about 25 pmol/cm$^2$, from about 25 pmol/cm$^2$ to about 50 pmol/cm$^2$, or from about 50 pmol/cm$^2$ to about 100 pmol/cm$^2$.

Suitable synthetic substrates include polymeric materials. Suitable polymeric materials include, e.g., materials described in, e.g., U.S. Patent Publication No. 2007/0026518, U.S. Patent Publication No. 2004/0001892, and U.S. Pat. No. 5,863,650, each of which is incorporated by reference herein for disclosure relating to synthetic substrates. For example, suitable substrates include interpenetrating polymer networks (IPNs); a synthetic hydrogel; a semi-interpenetrating polymer network (sIPN); a thermo-responsive polymer; and the like. For example, in some embodiments, a synthetic substrate comprises a co-polymer of polyacrylamide and poly (ethylene glycol) (PEG). In some embodiments, the synthetic substrate comprises a co-polymer of polyacrylamide and PEG, and further comprises acrylic acid.

A subject synthetic cell platform can be in any of a variety of forms, e.g., a 3-dimensional form (e.g., suitable for implanting into a tissue; or suitable as a synthetic tissue, for implanting into a recipient individual); a flat surface (e.g., suitable for coating onto the surface of an implantable device, such as an intravascular stent, an artificial joint, a scaffold, etc.); and the like.

In some embodiments, a subject synthetic cell platform comprises one or more mammalian cells bound thereto; and is useful for, e.g., introducing the cells into a recipient individual (e.g., a mammalian subject). In other embodiments, a subject synthetic cell platform is contacted in vitro with one or more mammalian cells; and the cells are cultured with the synthetic cell platform in vitro. In other embodiments, mammalian cells are cultured with a subject synthetic cell platform in vitro, then the cultured cells, which remain associated with the platform, and introduced into a recipient individual.

In some embodiments, a subject synthetic cell platform without any bound mammalian cells is implanted into a recipient individual, where the synthetic cell platform comprises one or more species of peptides that recruit one or more cell types to the site of implantation.

In some embodiments, a subject synthetic cell platform without any bound mammalian cells is coated onto the surface of an implantable device, forming a coated device. When the coated device is implanted into a recipient individual, the peptide present in the cell platform coated onto the device recruits one or more cell types (e.g., endogenous cells present in the individual) to the site of implantation. A subject synthetic cell platform can be coated onto a device comprising any of a variety of materials, including, but not limited to, plastics, including any biocompatible plastic; glass, e.g., silicon dioxide, and the like; metals, e.g., titanium; metal alloys, e.g., nickel titanium, etc.; or any other material that can be implanted into a recipient subject (e.g., a human) without causing substantial adverse effects. In some embodiments, e.g., a subject synthetic cell platform is coated onto a stent, where the peptide in the synthetic cell platform recruits endothelial precursors.

The present invention thus provides an implantable device comprising a surface and a subject synthetic cell platform coated onto the surface, forming a coated implantable device.

Stem Cells and Progenitor Cells

Cells that are suitable for culturing on a subject cell platform and/or including with a subject cell culture platform (e.g., to form an implantable cell composition) include, but are not limited to, stem cells, e.g., hematopoietic stem cells, embryonic stem cells, mesenchymal stem cells, neural stem cells, epidermal stem cells, endothelial stem cells, gastrointestinal stem cells, liver stem cells, cord blood stem cells, amniotic fluid stem cells, skeletal muscle stem cells, smooth muscle stem cells (e.g., cardiac smooth muscle stem cells), pancreatic stem cells, olfactory stem cells, hematopoietic stem cells, induced pluripotent stem cells; and the like; as well as differentiated cells that can be cultured in vitro and used in a therapeutic regimen, where such cells include, but are not limited to, keratinocytes, adipocytes, cardiomyocytes, pancreatic islet cells, retinal cells, and the like. The cell that is used will depend in part on the nature of the disorder or condition to be treated.

Suitable human embryonic stem (ES) cells include, but are not limited to, any of a variety of available human ES lines, e.g., BG01(hESBGN-01), BG02 (hESBGN-02), BG03 (hES-BGN-03) (BresaGen, Inc.; Athens, Ga.); SA01 (Sahlgrenska 1), SA02 (Sahlgrenska 2) (Cellartis AB; Goeteborg, Sweden); ES01 (HES-1), ES01 (HES-2), ES03 (HES-3), ES04 (HES-4), ES05 (HES-5), ES06 (HES-6) (ES Cell International; Singapore); UC01 (HSF-1), UC06 (HSF-6) (University of California, San Francisco; San Francisco, Calif.); WA01 (H1), WA07 (H7), WA09 (H9), WA13 (H13), WA14 (H14) (Wisconsin Alumni Research Foundation; WARF; Madison, Wis.). Cell line designations are given as the National Institutes of Health (NIH) code, followed in parentheses by the provider code. See, e.g., U.S. Pat. No. 6,875,607.

Suitable human ES cell lines can be positive for one, two, three, four, five, six, or all seven of the following markers: stage-specific embryonic antigen-3 (SSEA-3); SSEA-4; TRA 1-60; TRA 1-81; Oct-4; GCTM-2; and alkaline phosphatase.

Hematopoietic stem cells (HSCs) are mesoderm-derived cells that can be isolated from bone marrow, blood, cord blood, fetal liver and yolk sac. HSCs are characterized as $CD34^+$ and $CD3^-$. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

Mesenchymal stem cells (MSC), originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

An induced pluripotent stem (iPS) cells is a pluripotent stem cell induced from a somatic cell, e.g., a differentiated somatic cell. iPS cells are capable of self-renewal and differentiation into cell fate-committed stem cells, including neural stem cells, as well as various types of mature cells.

iPS cells can be generated from somatic cells, including skin fibroblasts, using, e.g., known methods. iPS cells produce and express on their cell surface one or more of the following cell surface antigens: SSEA-3, SSEA-4, TRA-1-60, TRA-1-81, TRA-2-49/6E, and Nanog. In some embodiments, iPS cells produce and express on their cell surface SSEA-3, SSEA-4, TRA-1-60, TRA-1-81, TRA-2-49/6E, and Nanog. iPS cells express one or more of the following genes: Oct-3/4, Sox2, Nanog, GDF3, REX1, FGF4, ESG1, DPPA2, DPPA4, and hTERT. In some embodiments, an iPS cell expresses Oct-3/4, Sox2, Nanog, GDF3, REX1, FGF4, ESG1, DPPA2, DPPA4, and hTERT. Methods of generating iPS are known in the art, and any such method can be used to generate iPS. See, e.g., Takahashi and Yamanaka (2006) Cell 126:663-676; Yamanaka et. al. (2007) Nature 448:313-7; Wernig et. al. (2007) Nature 448:318-24; Maherali (2007) Cell Stem Cell 1:55-70; Nakagawa et al. (2008) *Nat. Biotechnol.* 26:101; Takahashi et al. (2007) *Cell* 131:861; Takahashi et al. (2007) *Nat. Protoc.* 2:3081; and Okita et al. (2007 *Nature* 448:313.

iPS cells can be generated from somatic cells (e.g., skin fibroblasts) by genetically modifying the somatic cells with one or more expression constructs encoding Oct-3/4 and Sox2. In some embodiments, somatic cells are genetically modified with one or more expression constructs comprising nucleotide sequences encoding Oct-3/4, Sox2, c-myc, and Klf4. In some embodiments, somatic cells are genetically modified with one or more expression constructs comprising nucleotide sequences encoding Oct-4, Sox2, Nanog, and LIN28.

Implantable Compositions

As noted above, a subject synthetic cell culture platform can also be implanted into an individual along with one or more mammalian cells. As such, in some embodiments, a subject synthetic cell culture platform is also an implantable cell matrix. The present invention provide an implantable composition comprising a subject implantable cell matrix; and one or more mammalian cells (e.g., a stem cell; a progenitor cell; an undifferentiated progeny of a stem cell; a differentiated cell; a differentiated progeny of a stem cell; etc.). A subject implantable composition comprises one or more mammalian cells bound thereto, where "bound" refers to an association of the cells with the cell platform. A mammalian cell can be bound to the cell platform via interaction of a cell-binding peptide in the platform with a cell surface molecule on the mammalian cell. A subject implantable composition can comprise from about 10 to about $10^{10}$ mammalian cells, e.g., from about 10 to about $10^2$, from about $10^2$ to about $10^4$, from about $10^4$ to about $10^5$, from about $10^5$ to about $10^6$, from about $10^6$ to about $10^7$, from about $10^7$ to about $10^8$, from about $10^8$ to about $10^9$, or from about $10^9$ to about $10^{10}$ mammalian cells.

Methods of Culturing a Cell

The present invention provides methods of culturing a mammalian cell in vitro and/or in vivo. The methods generally involving contacting a mammalian cell (e.g., a stem cell, a progenitor cell, a differentiated progeny of a stem cell, a differentiated cell, etc.) with a subject synthetic cell platform. The contacting can occur in vitro and/or in vivo. In some embodiments, the mammalian cell remains in contact with (e.g., bound to) the cell platform. In other embodiments, the mammalian cell proliferates, and progeny of the bound cell are either in contact with the cell platform, or are unbound and are present in the cell culture medium (e.g., where the cell is cultured in vitro), or are unbound and are integrated into the tissue of a host (e.g., where the cell is introduced into an individual and is therefore in vivo). The present method of cell culture provides for culturing a cell in vitro without the need for a mouse or a human feeder layer of cells, i.e., a subject cell culture system and method is in the absence of a feeder layer of cells.

A suitable cell culture medium is used for in vitro culture, where a suitable cell culture medium can include one or more of a growth factor, vitamins, serum albumin (e.g., human serum albumin), and the like. In some embodiments, the cell culture medium lacks serum albumin.

In some embodiments, the peptide and the culture conditions provide for self-renewal of a stem cell.

In other embodiments, the peptide and the culture conditions provide for differentiation of a stem cell or progenitor cell into a differentiated cell.

For example, a stem cell can be induced to differentiate into a neuronal cell, an astrocyte, an oligodendrocyte, or a neuronal precursor cell. Markers of interest include, but are not limited to, β-tubulin III or microtubule-associated protein 2 (MAP-2), characteristic of neurons; glial fibrillary acidic protein (GFAP), present in astrocytes; galactocerebroside (GalC) or myelin basic protein (MBP); characteristic of oligodendrocytes; Nestin or Musashi, characteristic of neural precursors and other cells. A mature neuronal cell can be characterized by an ability to express one, two, three, four, five, six, seven, or all eight of: 160 kDa neuro-filament protein, MAP2ab, glutamate, synaptophysin, glutamic acid decarboxylase (GAD), tyrosine hydroxylase, GABA, and serotonin. The differentiated cells forming neural progenitor cells, neuron cells and/or glial cells can also be characterized by expressed markers characteristic of differentiating cells. The in vitro differentiated cell culture can be identified by detecting molecules such as markers of the neuroectodermal lineage, markers of neural progenitor cells, neurofilament proteins, MAP2ab, glutamate, synaptophysin, glutamic acid decarboxylase, GABA, serotonin, tyrosine hydroxylase, β-tubulin, β-tubulin III, GABA Aa2 receptor, glial fibrillary acidic protein (GFAP), 2',3'-cyclic nucleotide 3'-phosphodiesterase (CNPase), plp, DM-20, O4, and NG-2 staining.

As another example, a stem cell can be induced to differentiate into a hepatocyte. Hepatocyte lineage cells differentiated from stem cells can display one, two, three, or more, of the following markers: $\alpha_1$-antitrypsin (AAT) synthesis, albumin synthesis, asialoglycoprotein receptor (ASGR) expression, absence of α-fetoprotein, evidence of glycogen storage, evidence of cytochrome p450 activity, and evidence of glucose-6-phosphatase activity.

As another example, a stem cell can be induced to differentiate into a cardiomyocyte. In some embodiments, differentiation into a cardiomyocyte is ascertained by detecting cardiomyocyte-specific markers produced by the cell. For example, the cardiomyocytes express cardiac transcription factors, sarcomere proteins, and gap junction proteins. Suitable cardiomyocyte-specific proteins include, but are not limited to, cardiac troponin I, cardiac troponin-C, tropomyosin, caveolin-3, GATA-4, myosin heavy chain, myosin light chain-2a, myosin light chain-2v, ryanodine receptor, and atrial natriuretic factor. Whether a stem cell has differentiated into a cardiomyocyte can also be determined by detecting responsiveness to pharmacological agents such as β-adrenergic agonists (e.g., isoprenaline), adrenergic β-antagonists (e.g., esmolol), cholinergic agonists (e.g., carbochol), and the like. Whether a stem cell has differentiated into a cardiomyocyte can also be determined by detecting electrical activity of the cells. Electrical activity can be measured by various methods, including extracellular recording, intracellular recording (e.g., patch clamping), and use of voltage-sensitive dyes. Such methods are well known to those skilled in the art.

Cell Purification Methods

A subject synthetic cell platform can also be used to isolated (e.g., purify) a desired cell population, a desired cell type, etc. The present invention thus provides methods of isolating a desired cell type or cell population, the method generally involving contacting a mixed cell population that comprises a desired cell population or a desired cell type, under conditions that permit binding of the desired cell population or cell type to the synthetic cell platform; and separating bound from unbound cells. Multiple rounds of the binding and separating steps can be carried out. In addition, sequential binding and separating steps can be carried out with two or more synthetic cell platforms, each having covalently linked thereto a different peptide.

A subject method for isolating a desired cell population or a desired cell type results in a selected cell population, e.g., the selected cell population comprises at least about 50%, at least about 60%, at least about 70%, at least about 80%, at least about 90%, at least about 95%, at least about 98%, at least about 99%, or greater than 99%, of a desired cell type or cell population.

Desired cell populations/cell types can include, e.g., a differentiated cell (e.g., a cardiomyocyte, a hepatocyte, a HSC lineage cell, and the like); and a stem cell, e.g., an HSC, a neural stem cell, an ESC, an MSC, an iPS, an adult stem cell, and the like.

Therapeutic Methods

The present invention provides a method of treating a disorder in an individual in need thereof, the method generally involving implanting into the individual a subject implantable composition. The present invention provides a method of increasing survival of a cell implanted into a recipient individual, the method generally involving implanting into the recipient individual a cell bound to a subject cell platform. The present invention provides a method of inducing or promoting in vivo differentiation of a stem cell in a recipient individual, the method generally involving implanting into the recipient individual a stem cell bound to a subject cell platform.

A subject cell platform comprising a cell or progeny thereof is introduced into an individual at a site that is appropriate to the disorder being treated. Sites and modes of administration can include, e.g., implantation (e.g., of a subject platform comprising cardiomyocytes) into heart muscle; intravenous infusion (e.g., of a subject platform comprising HSCs or HSC lineage cells); implantation into the pancreas (e.g., of a subject platform comprising pancreatic islet cells); intramuscular injection (e.g., of a subject platform comprising skeletal muscle or muscle progenitor cells); intracranial implantation (e.g., of a subject platform comprising neural cells or glial cells); intraocular implantation (e.g., of a subject platform comprising neural cells or glial cells); intrathecal implantation (e.g., of a subject platform comprising neural cells or glial cells); and the like.

An "effective amount" of a subject synthetic cell platform comprising cells or progeny is an amount that, when administered to an individual in one or more doses, provides a therapeutic effect, e.g., provides for introduction into the individual of a sufficient number of cells to provide for a therapeutic effect. An effective number of cells or progeny thereof can range from about $10^3$ cells to about $10^9$ cells, e.g., from about $10^3$ cells to about $10^4$ cells, from about $10^4$ cells to about $10^5$ cells, from about $10^5$ cells to about $10^6$ cells, from about $10^6$ cells to about $10^7$ cells, from about $10^7$ cells to about $10^8$ cells, or from about $10^8$ cells to about $10^9$ cells.

For example, where a subject synthetic cell platform comprises pancreatic islet cells, an effective amount of a subject synthetic cell platform is an amount that includes pancreatic islet cell in cell numbers that are effective to reduce a blood glucose level in an individual by at least about 10%, at least about 15%, at least about 20%, at least about 25%, at least about 30%, at least about 40%, or at least about 50% when compared to the blood glucose levels in the absence of the cells. In some embodiments, effective number of HLA homozygous pancreatic islet cells is a number that is effective to reduce blood glucose levels to a normal range. Normal blood glucose levels are typically in the range of from about 70 mg/dL to about 110 mg/dL before a meal (e.g., a fasting blood glucose level); and less than 120 mg/dL 2 hours after a meal.

A subject cell platform increases in vivo survival of a cell bound thereto in a recipient individual. For example, a subject implantable composition (a subject cell platform having bound thereto a mammalian cell) provides for an at least about 10%, at least about 20%, at least about 30%, at least about 50%, at least about 75%, at least about 100% (or 2 fold), at least about 2.5 fold, at least about 5 fold, at least about 7.5 fold, at least about 10-fold, or greater, increase in the length of time the cell survives in the recipient individual, compared to the length of time the cell would survive in the individual in the absence of the cell platform.

In some embodiments, a subject cell platform increases in vivo proliferation of a cell bound thereto in a recipient individual. For example, a subject implantable composition (a subject cell platform having bound thereto a mammalian cell) provides for an at least about 10%, at least about 20%, at least about 30%, at least about 50%, at least about 75%, at least about 100% (or 2 fold), at least about 2.5 fold, at least about 5 fold, at least about 7.5 fold, at least about 10-fold, or greater, increase in the number of cells generated by a single implanted cell in the recipient individual, compared to the number cells generated by the cell in the individual in the absence of the cell platform.

In some embodiments, a subject cell platform increases in vivo self renewal of a stem cell bound thereto in a recipient individual. For example, a subject implantable composition (a subject cell platform having bound thereto a mammalian cell) provides for an at least about 10%, at least about 20%, at least about 30%, at least about 50%, at least about 75%, at least about 100% (or 2 fold), at least about 2.5 fold, at least about 5 fold, at least about 7.5 fold, at least about 10-fold, or greater, increase in self renewal of an implanted stem cell in the recipient individual, compared to the degree of self renewal of the stem cell in the individual in the absence of the cell platform.

In some embodiments, a subject cell platform promotes in vivo differentiation of a stem cell in a recipient individual. For example, a subject implantable composition (a subject cell platform having bound thereto a mammalian cell) provides for differentiation of a stem cell in vivo in a recipient individual, where the stem cell gives rise to one or more differentiated cell types in the recipient individual.

Subjects Suitable for Treatment

Subjects suitable for treatment with a subject method include individuals who have been diagnosed as having a blood cell cancer (e.g., a leukemia); individuals who have been diagnosed with AIDS; individuals with sickle cell anemia; individuals with an immune disorder, e.g., an acquired immunodeficiency, a genetic immunodeficiency; individuals with Type 1 diabetes; individuals with a nervous system disorder such as Alzheimer's disease, Parkinson's disease, Huntington's disease, Lou Gehrig's disease, spinal cord injury, stroke, etc.; individuals with a liver disorder such as hepatitis, cirrhosis, a metabolic disorder affecting the liver or central nervous system (e.g., lysosomal storage disease); individuals with a disorder of the cartilage or bone, e.g., individuals requiring joint replacement, individuals with osteoarthritis, individuals with osteoporosis, etc.; individuals with a cardiac disorder, e.g., myocardial infarction, coronary artery disease, or other disorder resulting in ischemic cardiac tissue; individuals with renal disorders, e.g., kidney failure (e.g., individuals on kidney dialysis); individuals with skeletal muscle disorders, such as muscular dystrophy; and individuals with a lung disorder such as emphysema, pulmonary fibrosis, idiopathic pulmonary fibrosis, etc.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Generation and Characterization of Synthetic Cell Platforms

This work was carried out with a synthetic material with highly modular ligand-presentation capabilities. Furthermore, the base material exhibits reduced non-specific interactions with constituents of the biologic environment (e.g., proteins, lipids, cells). As a first step toward creating such a platform technology, interfacial interpenetrating polymer networks (IPNs) were developed that are synthesized by sequential photoinitiated free-radical polymerization of an ultrathin layer of polyacrylamide followed by a secondary photoinitiation step using poly(ethylene glycol)-based monomers to create the network (FIG. 1)[29, 30, 41] Polyacrylamide, p(AAm), and poly(ethylene glycol), pEG, are hydrophilic polymers that have demonstrated low protein, cell, and bacterial binding characteristics, and are excellent materials for precise control of cell behavior. These IPN layers based on pAAm and pEG (p(AAm-co-EG)] have been grafted to both metal oxides (e.g., $SiO_2$, $TiO_2$) and polymers (e.g., tissue culture poly(styrene) and poly(ethylene terapthalate), i.e. PET). Characterization of the IPNs by contact angle goniometry, spectroscopic ellipsometry, x-ray photoelectron spectroscopy, and static secondary ion mass spectrometry has confirmed the formation of an interfacial IPN that resists protein adsorption and cell adhesion.[29, 30, 41, 58] When the p(AAm-co-EG/AAc) IPN is functionalized with the right bioactive ligand, it promotes cell adhesion from a non-fouling platform, which is ideal for the cell culture systems in this work.

FIG. 1. Schematic of the biomimetic interpenetrating polymer network. An acrylamide layer is polymerized from the surface, and subsequent polymerization of an interpenetrating polyethylene glycol network makes the surface resistant to fouling/protein adsorption. Finally, the surface can be decorated with bioactive peptides or proteins for bioactive cell engagement.

Specific cell-binding surfaces were generated by developing a high throughput system using the p(AAm-co-EG/AAc) IPN grafted to polystyrene 24-well and 96-well plates to generate a library of peptide modified surfaces of different types and densities (>6500 independent surfaces were created).[64] IPNs were modified with both single ligands and ligand blends to study the correlation between a simple metric, ligand-receptor adhesion strength, and cell behavior (e.g. the extent of matrix mineralization for osteoblasts in the cited work). The ligands studied included cell-binding [CG-GNGEPRGDTYRAY (bsp-RGD(15); SEQ ID NO:2), CGGEPRGDTYRA (bsp-RGD(12); SEQ ID NO:52), CGPRGDTY (bsp-RGD(8); SEQ ID NO:53), cyclic(CG-PRGDTYG) (c-bsp-RGD(9); SEQ ID NO:54), and CGPRGDTYG (bsp-RGD(9); SEQ ID NO:54)], heparin binding (CGGFHRRIKA; SEQ ID NO:56), and collagen binding (CGGDGEAG; SEQ ID NO:57) peptides, with the appropriate controls. Rat calvarial osteoblast (RCO) adhesion to peptide-modified IPN polystyrene was examined using a single-speed (600 RPM; ~58 g) and a multi-speed adhesion assay (200, 600, 1000, 2000, 2500, and 4000 RPM; ~6 to 2560 g).[5, 64] Cells were seeded at 10,000 cells/well, then incubated on the surfaces at 4° C. with total adhesion times of 18 min. After centrifugation, the number of attached cells was quantified fluorescently with the CyQuant reagent (Molecular Probes, Oreg.). Plates were read using a Spectramax Gemini XS fluorescent plate reader (Molecular Devices, Calif.).

Figure 2:
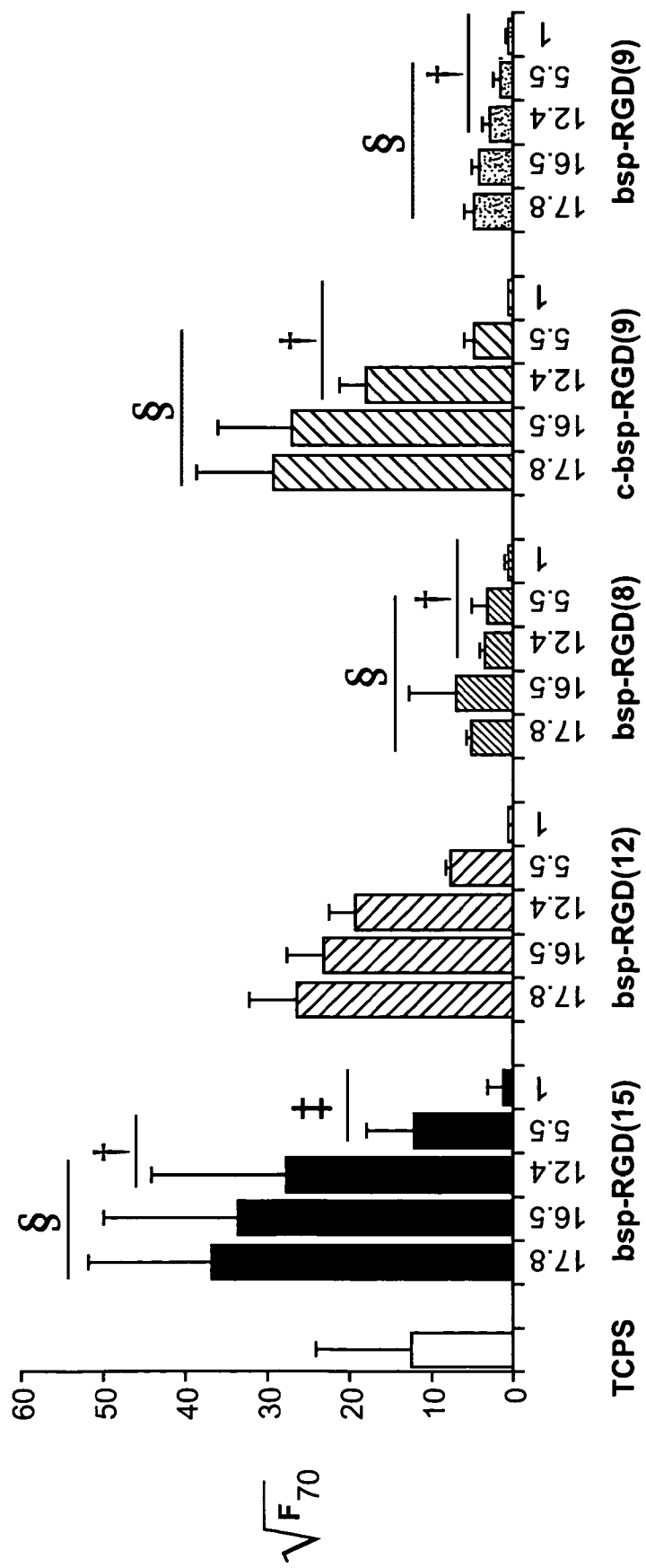
FIG. 2 depicts multi-speed adhesion assay results.

RCO adhesion strength scaled with ligand density (1-20 pmol/cm$^2$) and was dependent on ligand type (FIG. 2). Independent of ligand density, the percent/extent of matrix mineralization varied with ligand type with a ligand identity trend similar but not identical to adhesion.

FIG. 2. Multi-speed adhesion assay results: the detachment force adhesion parameter, $((F_{70})^{0.5}, g^{1.2})$, which was determined using a reverse normal distribution for each of the RGD-containing peptides arranged according to ligand with density in pmol/cm$^2$. TCPS with adsorbed serum proteins as reference. Modulation of cell adhesion via ligand type (w) and ligand density (pmol/cm$^2$). Note that with a proper choice of ligand type and ligand density, adhesion greater than tissue culture polystyrene (TCPS) can be achieved. (within each ligand group differences are grouped by symbol; $p<0.05$; Kruskal-Wallis with Dunn's posthoc test).

These studies demonstrate the dependence of cell differentiation (i.e., matrix mineralization for osteoblasts) on ligand type, ligand density, and adhesion strength. Significantly, it was demonstrated that short peptides containing the minimal RGD sequence do not in this case serve as effective ligands for integrin receptors, whereas the longer counterpart peptides with more amino acid sequence context do. Furthermore, the high throughput character of the method enabled the efficient investigation of multiple ligands at multiple densities and thereby provided an excellent tool for studying ligand-receptor interactions under normal cell culture conditions, capabilities essential for studying analogous interactions for hESCs.

IPN Surfaces Promote the Self-Renewal of Adult Neural Stem Cells

Neural stem cells are typically cultured on surfaces consisting of a poly(styrene)-based material with a passively adsorbed, animal-derived extracellular matrix (ECM) protein such as laminin or fibronectin.[67, 69] However, both animal- and human-derived ECM or proteins likely contain variable splice and glycoforms, offer limited micro- and nano-scale control of solid-phase signaling, pose problems with lot to lot variability, and otherwise present problems for therapeutic application.[16, 70] The ability of a peptide-modified interpenetrating polymer network (IPN) synthesized from acrylamide (AAm), poly(ethylene glycol) monomethyl ether monomethacrylate (pEGMA), and acrylic acid (AAc) monomers to support NSC growth was explored. NSCs isolated from the adult rat hippocampus,[67] were seeded onto 15 amino-acid bone sialoprotein RGD peptide [bsp-RGD(15)]-modified IPNs at various cell densities over four orders of magnitude. This peptide was chosen for its specificity for $\alpha_v\beta_3$ integrin,[64] since NSCs express $\beta_3$ integrins and since $\alpha_v\beta_3$ is known to engage the ECM molecule laminin.[71] Under proliferating media conditions (20 ng/ml fibroblast growth factor (FGF)-2), cell adhesion and morphology on the RGD surfaces were similar to that on laminin (FIG. 3a-b). By contrast, on surfaces with either lower or no bsp-RGD(15), cells did not adhere effectively (FIG. 3a-d) and resembled NSC growth in suspension as neurospheres.[72] Such cell aggregates provide less precise control over the cellular microenvironment, due in part to spatial gradients in signaling and nutrients and at times internal necrosis. The negative control bsp-RGE(15) (CGGNGEPRGETYRAY; SEQ ID NO:58), which differs from the bsp-RGD(15) peptide by only a methylene group, did not support attachment and thus highlighted the specificity of the NSC engagement with the peptide-modified IPN. IPNs modified with bsp-RGD(15) supported NSC proliferation in a ligand dose-dependent fashion, and IPNs with the highest bsp-RGD(15) density actually supported slightly faster cell proliferation than standard laminin-coated surfaces (FIG. 3e, $p<0.05$).

Figure 3:
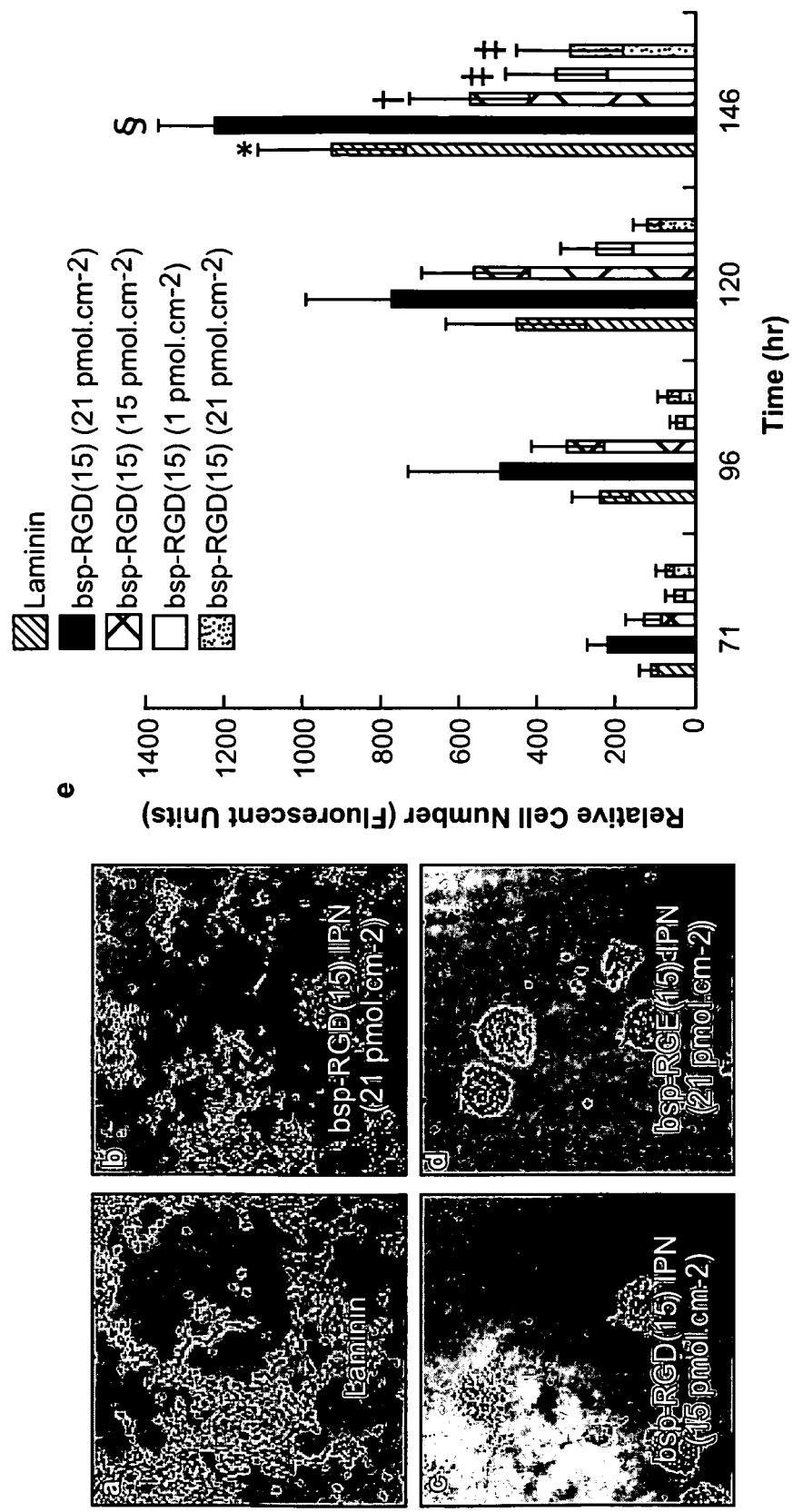
FIG. 3 depicts bright field images of neural stem cells grown on peptide-modified IPNs or laminin-I in proliferating media conditions.

FIG. 3. a-d) Bright field images of neural stem cells grown on peptide-modified IPNs or laminin-I in proliferating media conditions (1.2 nM FGF-2). e) Growth curves for proliferation of neural stem cells as assayed by a total nucleic acid stain. Data represent mean±standard deviation of 3-5 samples. Surfaces not in the same group (*, §, †, or ‡) were statistically different from one another ($p<0.05$; ANOVA between groups with Tukey-Kramer Honestly Significant Difference post-hoc test).

Figure 4:
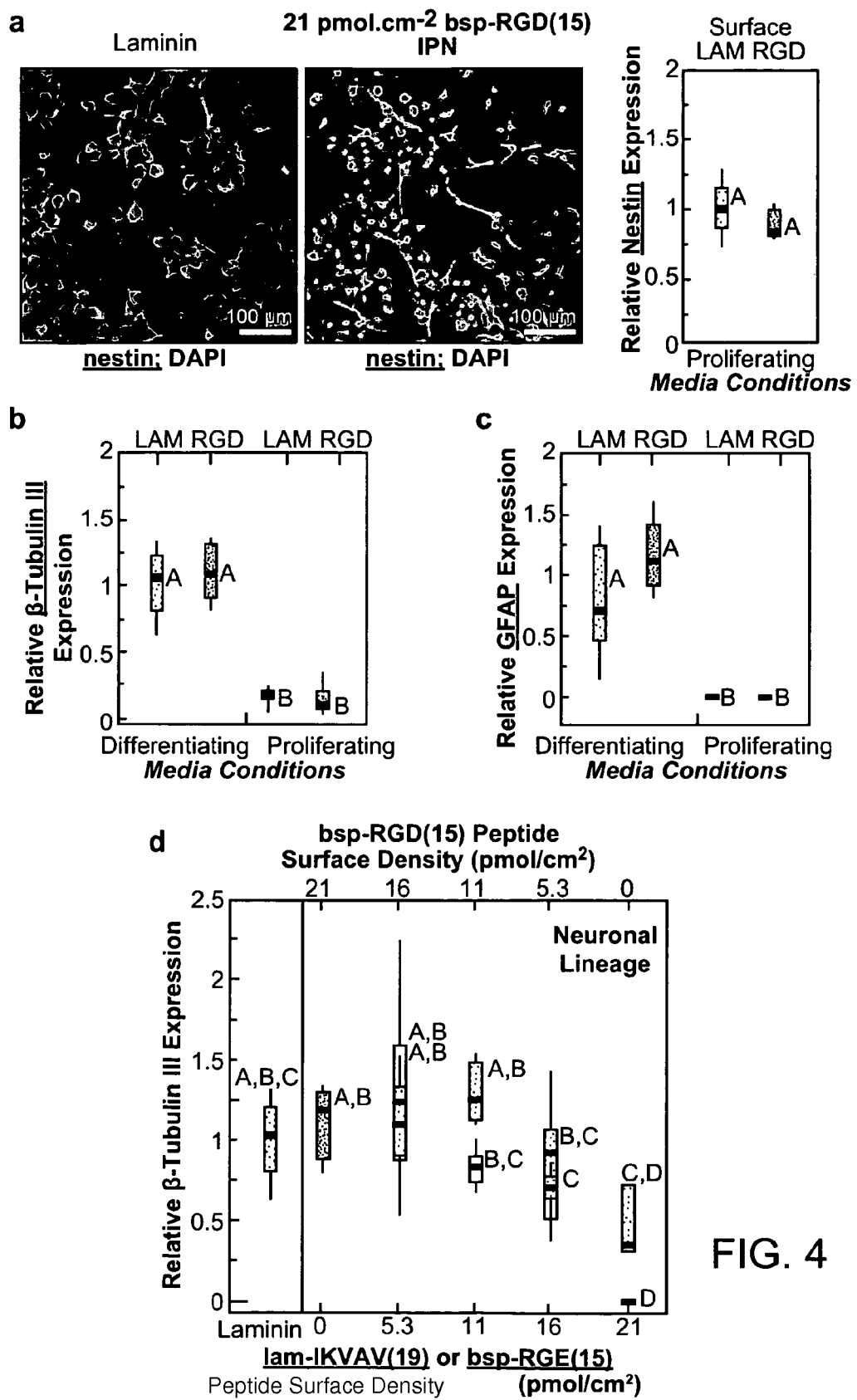
FIGS. 4A-D depict features of neural stem cells cultured in vitro.

To determine whether the cells were truly undergoing a process analogous to self-renewal, i.e. proliferation in the absence of differentiation, quantitative reverse transcription polymerase chain reaction (qRT-PCR) was employed to quantify the expression levels of nestin, a marker of an immature neural cell.[73] It was found that nestin expression levels on laminin and the synthetic hydrogel were the same (FIG. 4).

Stem cells are defined not only by their self-renewal but also their ability to undergo differentiation into one or more phenotypes. FGF-2 was removed and 0.2 µM retinoic acid and 5 µM forskolin, components known to induce tripotent cell differentiation, were added.[69] It was found that cells differentiated into neurons, astrocytes, and oligodendrocytes, the three major lineages of the nervous system (FIG. 4). Importantly, qRT-PCR (and immunostaining) revealed that the expression levels for markers of these three lineages were statistically indistinguishable on laminin and the synthetic hydrogel (FIG. 4). Therefore, the synthetic IPN, displaying an integrin-binding peptide, was able to substitute for laminin in supporting NSC proliferation and differentiation.

The effects of varying peptide identity and density on NSC differentiation were explored. The peptide motif Ile-Lys-Val-Ala-Val (IKVAV; SEQ ID NO:59) within laminin has been shown to promote neurite outgrowth from neurons.[74-76] It was hypothesized that incorporating a 19-mer peptide containing IKVAV (SEQ ID NO:59) may enhance NSC differentiation into neurons; however, it was found that as the IKVAV (SEQ ID NO:59) dosage increased, neuronal differentiation actually decreased (FIG. 4d).

FIG. 4. a) Immunofluorescence staining for the neural stem cell marker nestin (green) with stained nuclei (blue) in cells proliferating on laminin or 21 pmol.cm$^{-2}$ bsp-RGD(15) modified hydrogels (media conditions: 1.2 nM FGF-2). qRT- PCR demonstrates that statistically indistinguishable levels of nestin are expressed in cells on each surface. Likewise, qRT-PCR indicates that equal levels of b, the early neuronal marker β-tubulin III, and c, the mature astrocyte marker glial fibrillary acidic protein (GFAP) are expressed in cells on either surface under either proliferating or differentiating media conditions. The box plots summarize the distribution of points, where the thick line signifies the median and the ends of the box are the 25th and 75th quartiles. Within each plot, levels not connected by same letter are significantly different (p<0.05). d) As the density of bsp-RGD(15) was decreased and bsp-RGE(15) was increased, neuronal differentiation decreased. Furthermore, as bsp-RGD(15) was decreased and lam-IKVAV(19) (SEQ ID NO:59) increased, neuronal marker expression also decreased.

Example 2

Bacterial Peptide Display and Selection to Identify Novel Cell-Binding Peptides

As described above, bacterial display technology is particularly advantageous, since this approach enables presentation of pendant peptides on an extended surface (i.e. the bacterial cell) at densities that can be well-controlled within the range of 1,000-10,000 peptides/bacterial cell.[77] To accomplish this, a novel bacterial display scaffold was developed that enables identification of peptides that retain their ability to bind to their target receptor, even when removed from the bacterial surface scaffold protein used for their isolation. In other words, peptides discovered by this approach are ideally suited for materials functionalization through grafting. This new display system enables presentation of linear or disulfide constrained peptides on the surface of bacteria as N- or C-terminal fusions to a circularly permuted variant of outer membrane protein OmpX (CPX), rather than as insertion fusions. A panel of fluorescent libraries of linear and constrained peptide libraries displayed as either N- or C-terminal fusions to CPX was constructed. These libraries are typically composed of >10$^9$ independent peptide sequences/clones. Co-expression of a FACS optimized green fluorescent protein provides an intrinsic label that enables library screening using FACS, and streamlined analysis of isolated clones.[78]

Figure 5:
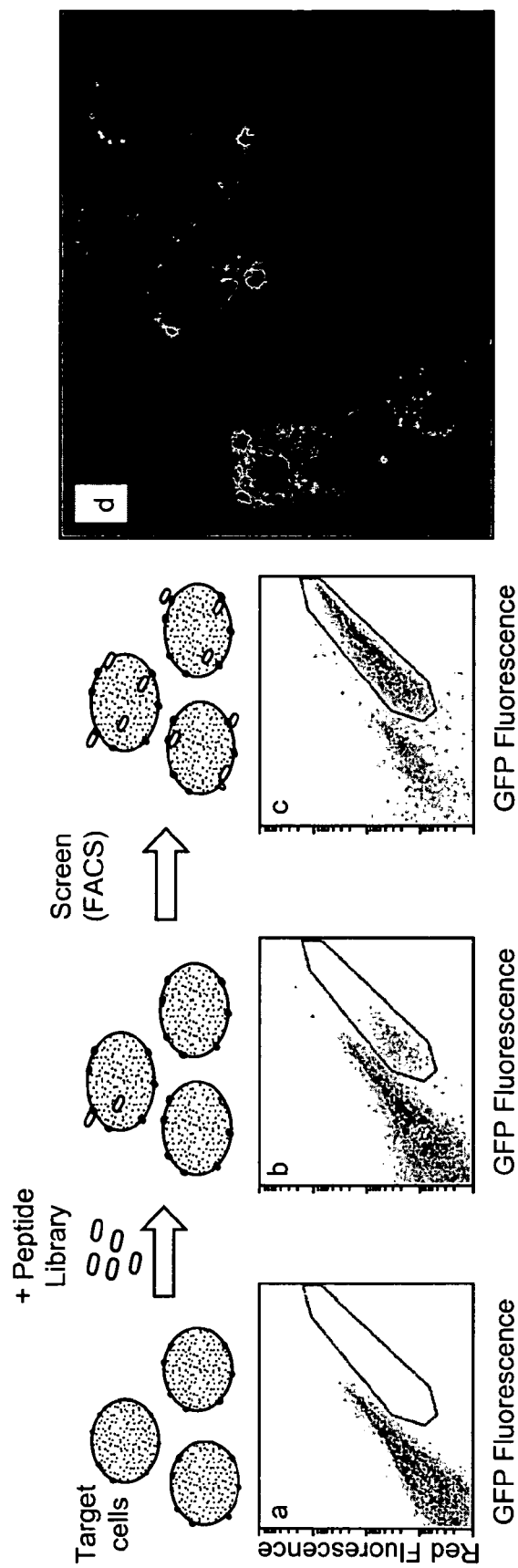
FIG. 5 depicts isolation of cell-specific peptides using bacterial display.

FIG. 5. Isolation of Cell-Specific Peptides Using Bacterial Display. Target cells were incubated with a peptide library displayed on the surface of bacteria (which are expressing GFP intracellularly and are therefore fluorescent). The cells bound to bacteria were thus rendered/labeled fluorescent and were sorted by FACS, and bound bacteria were recovered by growth for sequence analysis. Flow cytometric analysis of target cell fluorescence is shown a) in the absence of bacteria, b) after incubation with the fluorescent bacterial library, and c) after incubation with an individual binding clone isolated from the library. Red auto-fluorescence was also measured to provide improved discrimination of the target cells in the polygon gate. d) Overlaid phase contrast and fluorescence image of bacteria bound to a target cell surface.

It has been demonstrated that bacterial display methodology is highly effective in identifying peptides that recognize tumor cell and erythrocyte surface antigens. In both cases, isolated peptides: i) were specific for their intended target cell, ii) could subsequently be chemically synthesized and used to functionalize materials surfaces (e.g. polystyrene nanoparticles), and iii) retained binding function even when chemically synthesized and tested outside of the context of the bacterial display scaffold. The identification of peptides that recognize both adherent and suspended cells is straight-forward (FIG. 5). Target cells are mixed together with the library and washed several times, and the resulting fluorescently-labeled target cells (carrying bound bacteria) are recovered using FACS. Individual bacteria/peptide clones are isolated, and plasmid DNA is recovered/purified for sequencing to determine the identity of the displayed peptide. This full process can be completed in several days.

This technology has also been used to identify peptides capable of binding to the surface of adult neural stem cells. Both N- and C-terminal peptide display libraries were screened on NSCs, with the first two rounds selected through centrifugal pelleting of NSCs to isolate bacterial clones displaying binding peptides, and the third round selected through FACS. Following the third round, numerous peptide clones were sequenced (~30 novel sequences determined to date). Importantly, a number contain RGD motifs, indicating that the technology likely isolated novel integrin ligands, whereas others intriguingly do not (FIG. 6a). A BLAST search did not reveal significant sequence identity to other known mammalian proteins in most peptides, indicating the identification of novel cell-binding ligands. Furthermore, to confirm the ability of the peptides to mediate binding, clonal bacteria populations presenting each peptide were mixed with NSCs and subjected to flow cytometry analysis, and results indicate that the displayed peptides mediate specific binding (FIG. 6b-c).

Figure 6:
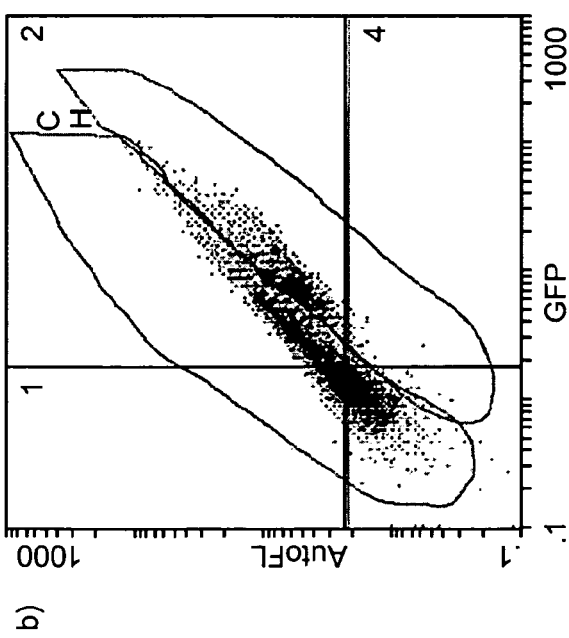
FIG. 6a depicts peptides.
FIGS. 6b and 6c depict isolation of neural stem cell binding bacterial clones. The peptides depicted in FIG. 6a are: WWCDMRGDSRCSG (SEQ ID NO:32); YMCMSRGDATCDV (SEQ ID NO:17); QCCQLRGDAVCNC (SEQ ID NO:26); WVCNKLGVY-ACEY (SEQ ID NO:28); LECTERGDFNCFV (SEQ ID NO:20); AND ESCWYQIMYKCAN (SEQ ID NO:15).
Figure 6:
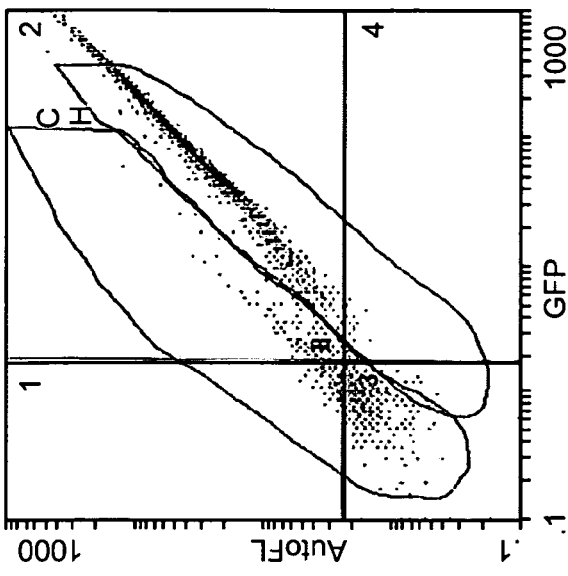

FIG. 6. Isolation of Neural Stem Cell Binding Bacterial Clones. a) Bacterial peptide display libraries were screened as in FIGS. 5, and 6 representative clones (of ~30 sequenced to date) are shown. Three have RGD sequences (number 1 with homology to thrombospondin and number 3 with homology to collagen IV), and three do not. b) Individual clonal bacterial populations were validated for the ability to bind to NSCs. Negative control flow cytometry data show diagonal fluorescence (with some potential nonspecific binding not observed in FIG. 5). c) However, all clones analyzed to date exhibit strong binding to NSCs, as indicated by the presence of a strongly GFP+ population (relative to their autofluorescence) of NSCs with adherent bacteria. The representative data shown are for bacteria presenting peptide 1 from part a).

Example 3 hESCs Grown on Synthetic ECMs

The work with osteoprogenitors (FIG. 2) and neural stem cells (FIGS. 3-4) establishes the strong potential of IPN surfaces to control cell function.

The HSF6 hESC cell line, a federally approved line derived at UCSF[80], was used. This line was cultured on both mouse embryonic fibroblast (MEF) feeder cells as well as a semi-interpenetrating network hydrogel system. MEFs (from CF-1 mice, Charles River) were mitotically inactivated via gamma irradiation and cultured on gelatin (collagen-derived) adsorbed to plasma-treated polystyrene (Falcon). Complete culture media (KSR) consisted of: Knockout-DMEM (Invitrogen), 20% Knockout Serum Replacement (Invitrogen), 2 mM Glutamine (Invitrogen), 0.1 mM non-essential amino acids (NEAA)(Invitrogen), 0.1 mM β-mercaptoethanol (Sigma), and 4 ng/mL FGF-2 (R&D Systems). When hESCs were cultured on sIPNs, colonies were maintained in conditioned KSR media, generated by pre-incubating KSR on MEFs for 24 hours such that the hESCs could be exposed to signaling molecules secreted from MEFs.

To compare the ability of sIPNs vs. MEFs to support the self-renewal of hESCs, several characteristics were assessed:

colony attachment, colony morphology, cell viability, and the presence of hESC markers. Morphological changes were one of the early indicators of differentiation. Undifferentiated hESC colonies that were cultured on MEFs (positive control) are shown in FIG. 7a-b. Undifferentiated hESCs exhibited a high nucleus to cytoplasm ratio, formed tightly packed colonies with defined colony borders, and expressed embryonic stem cell markers such as the transcription factor Oct4 and the surface carbohydrate moieties stage-specific embryonic antigen SSEA-3 and SSEA-4 (not shown). FIG. 7e-f shows that very few hESC colonies were able to attach to a negative control gelatin-coated surface. Also, the few that attached spontaneously differentiated, resulting in indistinct colony borders and larger, spindly, fibroblast-like cells that migrated away from the colony. In contrast, hESCs cultured on the sIPNs (FIG. 7c-d) exhibited morphologies similar to those of undifferentiated hESCs cultured on MEFs (FIG. 7a-b), where colonies had distinct borders with small (~10 μM diameter) and tightly packed cells.

Figure 7:
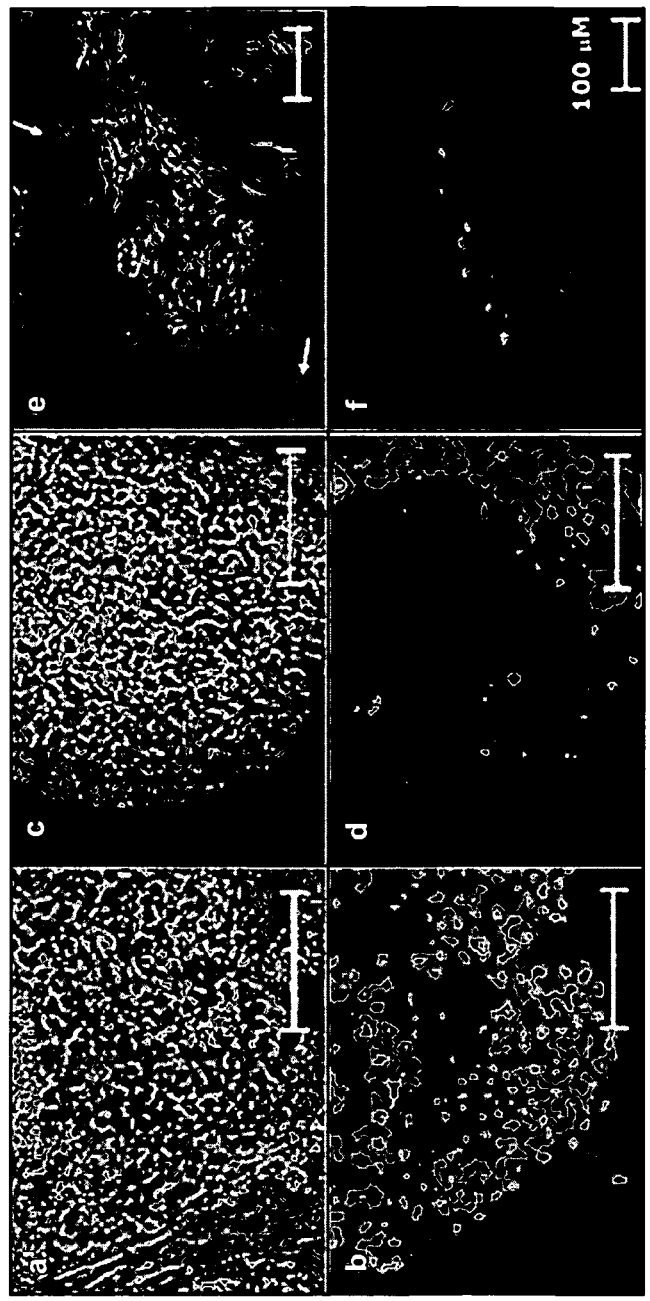
FIGS. 7A-F depict morphology and Oct4 immunofluorescence of hESCs cultured in vitro.

FIG. 7. Morphology and Oct4 immunofluorescence of hESCs at Day 5. a, b) hESCs cultured on MEFs exhibited small, tightly packed cells with distinct colony borders. c, d) hESCs cultured on sIPN exhibited similar morphologies when compared to a, b. e, 1) hESCs cultured on gelatin-adsorbed polystyrene exhibited morphologies of spontaneously differentiating cells, with spindle-shaped cells and indistinct colony borders. Oct4 was present in some cells under all three conditions. However, note that in hESCs cultured on polystyrene (f), white arrows point to cells beyond the colony edge which were not positive for Oct4.

Immunofluorescence staining was conducted to assess whether cells retained markers of undifferentiated hESCs. The POU family transcription factor Oct4 is a highly specific marker, and necessary protein, for undifferentiated hESCs, and SSEA-4 is a glycolipid cell surface antigen strongly expressed in undifferentiated hESCs.[18] Results showed the presence of Oct4 (FIG. 7) and SSEA-4 in cultures of all three conditions at day 5. For the hESCs cultured on gelatin-adsorbed polystyrene (FIG. 7f), cells beyond the edge of the colony were not positive for Oct4, indicating that they had spontaneously differentiated. Under these suboptimal conditions, some hESCs in the colony cores did not yet completely lose their undifferentiated characteristics after 5 days.[81] By comparison, the hESCs cultured on sIPNs (FIG. 7d) exhibited a tight border and were positive for Oct4. Interestingly, the Oct4 fluorescence appeared somewhat diffuse in the center of the colony, a result attributed to competing fluorescence from out-of-focus cell layers in the colony.

To take an important step towards a fully chemically defined microenvironment, H1 hES cells were cultured,[17] for which a serum-free, defined medium has been developed. In addition, this feeder-free system involves culturing cells on tissue culture polystyrene coated with Matrigel, an ECM mixture of predominantly fibronectin, collagen IV, and heparan sulfate.[19, 82] Cells were grown in non-conditioned, serum free medium (NC-SFM), which consists of X-VIVO 10 (Cambrex, Walkersville, Md.) medium supplemented with 0.5 ng/mL TGF-β1 and 80 ng/mL FGF-2 (Invitrogen). This medium and substrate, developed by Geron Corp., have been found to support hESC self-renewal to the same to the same extent as MEF feeders.[82] Cells are passaged by mechanical disruption, most often after brief incubation in collagenase IV.

Cultures on Matrigel consisted of Oct4+ hESC colonies interspersed with differentiated, Oct4-stromal cells derived from the hESCs, as previously described (note that the hESCs can be selectively passaged by timing the enzymatic digest).[82] H1 cells were also cultured in the NC-SFM on bsp-RGD(15) conjugated IPN surfaces (identical to those in FIGS. 3-4). Cultures were strikingly similar to those cultured on Matrigel, with high Oct4 levels in large hESC colonies. By contrast, cells predominantly died on bsp-RGE(15) IPN surfaces and differentiated on polystyrene. Both HSF6 cells on the sIPN (FIG. 7) and H1 cells on the IPN were able to maintain Oct4 expression for 3 passages (~10 days).

Example 4

Screening Peptide Libraries for Activation of Cell Signaling Pathways

In general, soluble growth factor signals synergistically interact with immobilized matrix signals to regulate cell function.[88, 89] However, even if an immobilized motif binds to a cell surface, it may not actively stimulate cellular signaling pathways. Therefore, while the peptides isolated as described above likely contain a rich repertoire of binding motifs for tissue engineering applications, it would be highly advantageous to select them for bioactivity.

The phosphoinositide-3 kinase (PI 3-kinase) signaling pathway, which can be activated by numerous cell surface receptors, has been implicated in regulating cell survival and proliferation in a number of contexts.[90-92] After ligation and activation of canonical receptors, phosphorylation of receptor tails on specific tyrosine residues recruits PI 3-kinase to the cell surface to phosphorylate phosphoinositide lipids. These lipids then recruit several kinases, including PDK1 and Akt. Phosphorylation of the latter by the former activates Akt, which then modulates a number of downstream effectors (such as Bad, mTOR, forkhead transcription factors, GSK-3β, and others) important in cell survival, proliferation, and other functions.[92, 93] Very importantly, PI 3-kinase and Akt signaling may be a general pathway important for stem cell proliferation and self-renewal. It has previously been found that their signaling (but not MAPK signaling) is required for self-renewal, as PI3-kinase/Akt inhibition leads to ES differentiation.[94, 95] Likewise, it has been found that PI 3-kinase and Akt signaling is activated by numerous adult neural stem cell mitogens (FIG. 8a, c-g). Furthermore, growing neural stem cells on the biomimetic hydrogel displaying bsp-RGD (15) led to the activation of Akt to a greater extent than a surface displaying the negative control bsp-RGE(15) peptide (the same surfaces as in FIGS. 3-4). Finally, chemical or genetic inhibition of this pathway inhibits self-renewal, whereas overexpression of transducers in this pathway promotes self-renewal in a mitogen-independent fashion.

Fluorescence resonance energy transfer has served as the basis for high throughput drug screens,[96] and can be used to screen peptides. A FRET sensor of Akt activation has already been developed. Briefly, a donor cyan fluorescent protein (CFP) and acceptor yellow fluorescent protein (YFP) with an intervening Akt substrate peptide yields FRET signal changes with Akt signaling and phosphorylation.[6] This sensor is compatible with a high throughput, FACS-based screen.

Experimental Design: CFP and YFP mutants that are optimal FRET partners,[97] were recently identified in a review article as the optimal FRET partners in the field.[98] To further enhance the sensitivity of the existing Akt FRET sensor, the more sensitive CFP/YFP pair is used.[97] A hESC cell line stably expressing this enhanced Akt sensor is generated using a lentiviral vector system [99, 100] that has previously proven to be an effective vector for generating stable hESC cell lines.[101, 102]

The genes encoding the scaffold protein and successful binding peptides from are amplified by PCR, inserted into an otherwise identical expression plasmid that does not contain the GFP (which would interfere with FRET), and transformed into bacteria. The resulting bacterial library is incubated with the hESC line in suspension as described above, and after 5-30 minutes (as in FIG. 8e-f), cells are subjected to flow cytometry to screen for peptide clones capable of activating PI 3-kinase signaling in hESCs and thereby inducing a FRET signal. Additional such selection rounds may be conducted if necessary. This FRET-based FACS screen will cull the peptides to yield a smaller number of peptides capable of activating hESC-signal transduction.

Figure 8:
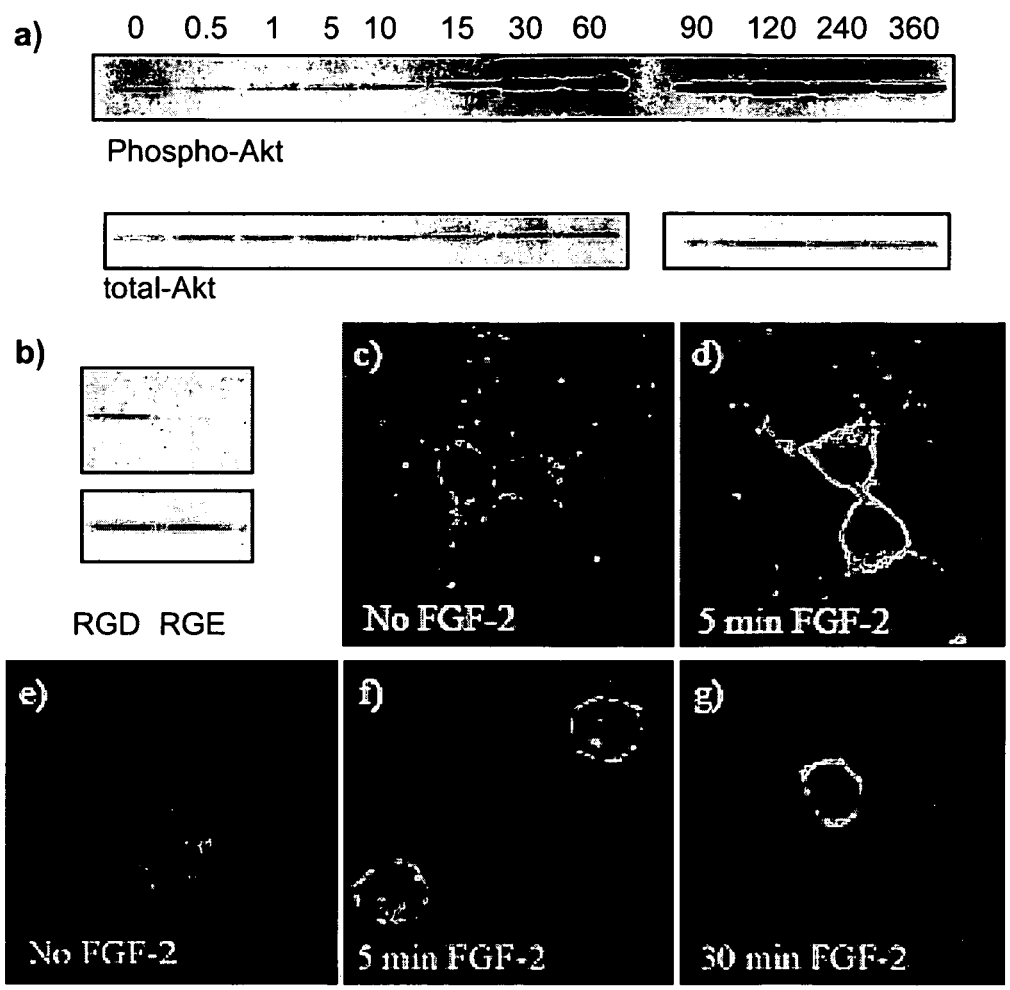
FIGS. 8A-G depict analysis of phosphorylated/activated Akt.

FIG. 8. Western blotting shows the level of phosphorylated/activated Akt (top rows) vs. total Akt (bottom rows) after a) stimulation with FGF-2 (minutes). b) Furthermore, higher levels of Akt are activated on RGD vs. RGE hydrogels. c) and d) Immunostaining for phospho-Akt shows Akt activation by FGF-2. Likewise relocalization of a PH-GFP genetic sensor to the cell surface acts as a sensor of PI 3-kinase signal activation after FGF-2 addition. An analogous genetic sensor of Akt based on FRET has been generated.[6]

Figure 9:
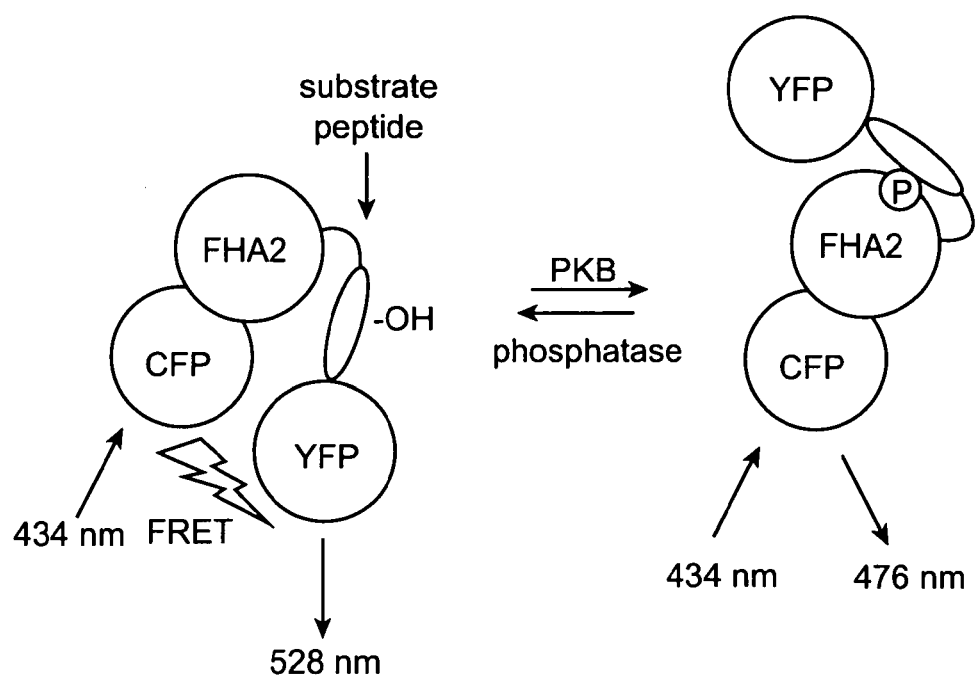
FIG. 9 is a schematic depiction of a BKAR sensor.

FIG. 9 is a schematic depiction of a Protein Kinase B (PKB) sensor (BKAR). Incorporation of selected peptides into a synthetic hydrogel can yield bioactive materials that efficiently promote long-term hES self-renewal.

About 20 chemically synthesized peptides (EZBiolabs, 10 mg synthesis scale, >90% purity) identified above are used, but with terminal Cys residues for attachment to the matrix.[64] The experimental system described above (FIGS. 1-4) is used to create IPNs on standard 48-well plates and subsequently graft these chemically synthesized peptides at various densities. Effective peptide densities for this work can range from 0 to 20 pmol/cm$^2$, showing myriad cell behavior such as cell attachment, spreading, focal contact formation, and proliferation requires ligand densities on solid 2D and hydrogel surfaces greater than approximately 1.5 fmol/cm$^2$ to 10 pmol/cm$^2$.[1, 28, 35, 38, 107, 108] These surface densities translate into ~1-100 nmol/cm$^3$, assuming a 10 nm thick slab of hydrogel.[107]

The centrifuge-based adhesion assay, which employed peptide-modified IPNs (FIG. 3), is used as a first test of the adhesive character of these peptides. Importantly, both cell adhesion strength and intracellular signaling have been observed to be directly proportional to the number of integrin-ligand bonds,[109, 110] Since the adhesion assay was developed to test initial adhesion events, assay times are kept short (<20 min), and experiments are conducted at 4° C., a standard experimental practice.[111] After seeding 10,000 cells/well from a 4° C. cell stock, each well is overfilled with 4° C. media. Overfilling ensures that any bubbles present at this stage can carefully be removed (aspirated), and results in each well being topped off with a 1-2 mm positive meniscus to ensure that air pockets will not be trapped in the wells after subsequent sealing (Titer-Tops adhesive film, Diversified Biotech, Inc). Assays are performed using an Eppendorf 5810R centrifuge equipped with a swinging bucket rotor fitted with microplate buckets (A-4-62-MTP) (effective radius 14.3 cm; possible detachment forces ≈6 to 2558 g). To prevent leakage, each swinging bucket is modified with a stainless steel support plate to replace the stock semi-rigid plastic supports and provide a flat, rigid surface for the inverted sample plates to press against without distortion. In addition, buckets are modified with a ≈2 mm thick membrane made of silicone elastomer positioned between the support plate and the inverted, taped microplate to further prevent well leakage.

Due to the short assay times required (<20 min), cells are first forced to the bottom of the wells to engage ligands by gently pre-spinning plates at a low force (5 min, 4° C., ~6 g). Pre-spinning forces less than 10 g do not significantly affect the subsequent force required to detach cells.[111] After pre-spinning, plates are incubated at 4° C. for 5 min in the centrifuge (total adhesion time, 18 min). Plates are then inverted, centered on top of the silicone elastomer and subjected to a ~57 g detachment force (600 RPM). Following cell detachment, the tape is quickly removed, and each well is gently aspirated. To prevent detached cells from resettling, plates remain inverted until the tape is removed. After aspiration, plates are frozen (−80° C.), and the total number of attached cells is quantified using CyQuant (FIG. 3). Running the assay without any rinsing steps to remove non-adherent cells eliminates the potential of well-to-well and plate-to-plate variation caused by uncontrolled hydrodynamic forces during rinses.[112]

Example 5

Screening Peptide Libraries for Neural Stem Cell Binding

Three different, validated peptide libraries were pooled to generate a large library (>10$^{10}$ independent clones) and were used for selection and screening.[79] These libraries include a random 15-mer (—X$_{15}$—) fused to either the N- or C-terminus of the CPX display scaffold and an N-terminal constrained library of the form X$_2$CX$_7$CX$_2$. The library has been made intrinsically fluorescent using a bicistronic expression vector to enable co-expression of a green fluorescent protein optimized for FACS.

The bacterial library was screened for binding peptides. For the first two cycles, screening was again conducted by co-sedimentation, where as many as 10$^8$ NSCs suspended via mechanical disruption in 0.5 mM EDTA as described[82] were incubated with 10$^{10}$ bacteria prior to several gentle centrifugations and rinses. The resulting mixture was added directly to bacterial media (LB) for expansion of the binding clones. The second cycle repeated this process with 10-fold fewer bacteria for higher stringency. In the third cycle, after incubation with 10$^6$ NSCs and washing, cells were sorted (as in FIGS. 5-6) using a DAKO-Cytomation MoFlo flow cytometer in the UC Berkeley Cancer Center to stringently isolate bacteria that are bound to NSCs. The resulting sorted bacteria were expanded. Plasmid DNA was isolated from a number of individual clones (at least 100)[79] and subjected to DNA sequencing to identify the peptide responsible for binding to the NSC surface.

Bacterial peptide display libraries were constructed, as described above, and tested for binding capacity to neural stem cells. Clonal populations of the bacterial peptide display libraries after the third round of selection were analyzed via flow cytometry to measure the binding capacity of the clones. Sequences of the clones were determined through DNA sequence of the plasmid expressed by the bacteria. Table 5 presents amino acid sequences of peptides and the binding capacity to NSCs of bacterial clones displaying the peptides.

TABLE 5

| Clone | % NSCs with Bacteria | Peptide Sequence |
| --- | --- | --- |
| 15-2 | 75.9 | DHKFGLVMLNKYAYAG (SEQ ID NO: 60) |

TABLE 5-continued

| Clone | % NSCs with Bacteria | Peptide Sequence |
|---|---|---|
| Co-3 | 75.7 | GGCRWYAKWVCVW (SEQ ID NO: 61) |
| Co-9 | 75.7 | SKCWGWTPYYCVA (SEQ ID NO: 62) |
| Co-22 | 75.6 | VWCGMFGKRRCVT (SEQ ID NO: 63) |
| 7C-21 | 75.5 | WNCIKGSSWACVW (SEQ ID NO: 64) |
| 7C-1 | 75.2 | WYCFREN KYVCVM (SEQ ID NO: 65) |
| Co-2 | 74.8 | WSCPKVNQYACFW (SEQ ID NO: 66) |
| Co-12 | 74.3 | WVCLWRHRGDCSI (SEQ ID NO: 67) |
| Co-1 | 73.8 | SLCAAYNRWACIW (SEQ ID NO: 68) |
| Co-10 | 72.7 | WRCLGDGYHACVR (SEQ ID NO: 69) |
| Co-11 | 72.7 | LECPGESKYYCIY (SEQ ID NO: 70) |
| Co-17 | 72.1 | WECAEESKFWCVF (SEQ ID NO: 71) |
| 7C-3 | 71.9 | WFCLLGRSAYCVR (SEQ ID NO: 72) |
| Co-16 | 71.9 | QGCAFVTYWACIF (SEQ ID NO: 73) |
| 7C-9 | 71.3 | KLCCFDKGYYCMR (SEQ ID NO: 74) |
| Co-18 | 71.3 | WWCKKPEYWYCIW (SEQ ID NO: 75) |
| Co-23 | 71.1 | LVCNRQNPWVCYI (SEQ ID NO: 76) |
| Co-15 | 70.9 | WVCNDLIHHFCVW (SEQ ID NO: 77) |
| Co-20 | 70.9 | RLCCWKTQYFCEI (SEQ ID NO: 78) |
| Co-21 | 70.9 | MYCERDSKYWCIH (SEQ ID NO: 79) |
| 15-32 | 70.4 | RRELVRMTDWVWVSG (SEQ ID NO: 80) |
| 15-6 | 70.2 | LEDAMGWALSWGHIW (SEQ ID NO: 81) |
| 7C-8 | 68.8 | WLCLDKNCMACVW (SEQ ID NO: 82) |
| 7C-17 | 67.8 | WLCKGSNKYMCEW (SEQ ID NO: 83) |
| Co-5 | 67.4 | WDCGKKNAWMCIW (SEQ ID NO: 84) |
| 7C-20 | 65.7 | WVCIWERFKSCNE (SEQ ID NO: 85) |
| 7C-5 | 65.6 | IWCGSRFGCWCKP (SEQ ID NO: 86) |
| 15-50 | 64.9 | GFVLVWSYTCRCWGK (SEQ ID NO: 87) |
| Co-13 | 64.8 | STCSWVSSYVCIM (SEQ ID NO: 88) |
| 7C-12 | 64.5 | FWCIRGEYWVCDR (SEQ ID NO: 89) |
| 15-16 | 63.9 | SDWSVLLSCERWYCI (SEQ ID NO: 90) |
| 15-52 | 63.3 | ESGLKVMCMKYYCMA (SEQ ID NO: 91) |
| 7C-4 | 62.0 | YMCMSRGDATCDV (SEQ ID NO: 92) |
| 7C-6 | 61.8 | GECFYYVMNTCVW (SEQ ID NO: 93) |
| 7C-24 | 61.7 | WWCDMRGDSRCSG (SEQ ID NO: 94) |
| Co-8 | 61.7 | WTWESAFAGRWEVGD (SEQ ID NO: 95) |
| 7C-2 | 55.2 | ESCWYQIMYKCAN (SEQ ID NO: 96) |
| 7C-14 | 54.5 | LNCAMYNACIW (SEQ ID NO: 97) |
| 7C-15 | 54.0 | QCCQLRGDAVCNC (SEQ ID NO: 98) |
| Co-19 | 50.6 | WQCGRFWCIHCLW (SEQ ID NO: 99) |
| 7C-7 | 47.8 | LECTERGDFNCFV (SEQ ID NO: 100) |
| 7C-22 | 46.9 | WMCSGVQPNACVW (SEQ ID NO: 101) |
| 7C-11 | 37.7 | LCCESYICALCHY (SEQ ID NO: 102) |
| 15-59 | 22.5 | DLCTYGHLWLGNGRP (SEQ ID NO: 103) |
| 7C-19 | 20.5 | WVCNKLGVYACEY (SEQ ID NO: 55) |

Figure 10:
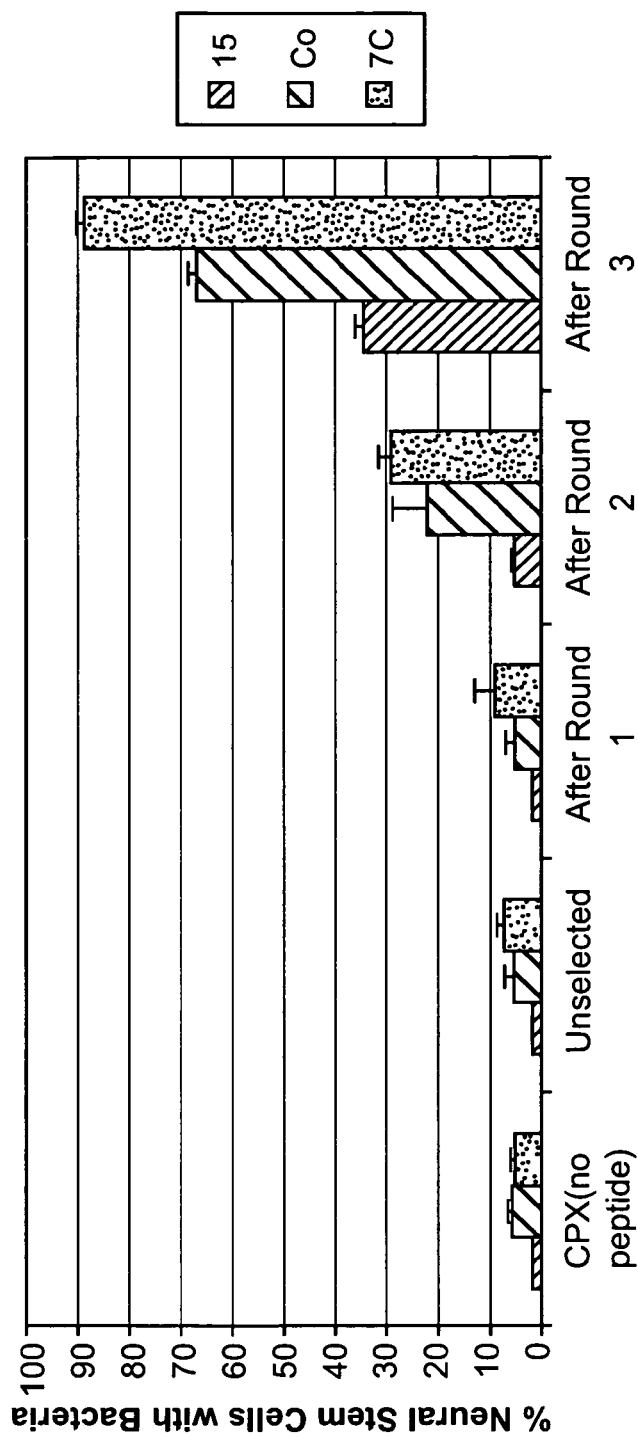
FIG. 10 depicts library population binding to neural stem cells after each round of selection.

The GFP-expressing bacterial peptide libraries from each round were incubated with the neural stem cells and the amount of bacteria bound to these cells was quantified via flow cytometry. A bacterial population only expressing the membrane protein CPX with no peptide was also tested in a similar manner. The data, shown in FIG. 10, indicate that after the second and third rounds of selection, the library population has a higher amount of bacteria binding to the neural stem cells compared to binding of bacteria with no peptide displayed.

Example 6

Screening Peptide Libraries for Embryonic Stem Cell Binding

The approach described in Example 5, above, is applied to hESCs. To provide an approach that yields peptides potentially suitable for hESCs cultured in both serum containing and serum free media, hES cell lines HSF6 (derived at UCSF, FIG. 7) and H1 (originally derived by Thomson et al.[17]) can be used.

In addition, throughout this work, benchmark control cell culture conditions consisted of culturing cells on surfaces coated with a 1:30 dilution of Matrigel (growth factor reduced, Becton Dickinson) in defined, non-conditioned, serum free medium (NC-SFM), as described.[82]

The bacterial library is screened for binding peptides. For the first two cycles, screening is again conducted by co-sedimentation, where as many as $10^8$ hESCs suspended via mechanical disruption in 0.5 mM EDTA as described[82] are incubated with $10^{10}$ bacteria prior to several gentle centrifugations and rinses. The resulting mixture is added directly to bacterial media (LB) for expansion of the binding clones. The second cycle repeats this process with 10-fold fewer bacteria for higher stringency. In the third cycle, after incubation with $10^6$ hESCs and washing, cells are sorted (as in FIGS. 5-6) using a DAKO-Cytomation MoFlo flow cytometer in the UC Berkeley Cancer Center to stringently isolate bacteria that are bound to hESCs. In addition, if needed, cells are sorted that both have bound, GFP+ bacteria and have high levels of expression of the hESC marker SSEA-4 (by using a primary antibody against this antigen followed by a Cy3-labeled secondary antibody,[82] prior to incubation with bacteria). The resulting sorted bacteria are expanded. Plasmid DNA is isolated from a number of individual clones (at least 100)[79] and subjected to DNA sequencing to identify the peptide responsible for binding to the hESC surface.

Example 7

Biomaterial Screening Through Analysis of NSC Attachment and Proliferation

Figure 11:
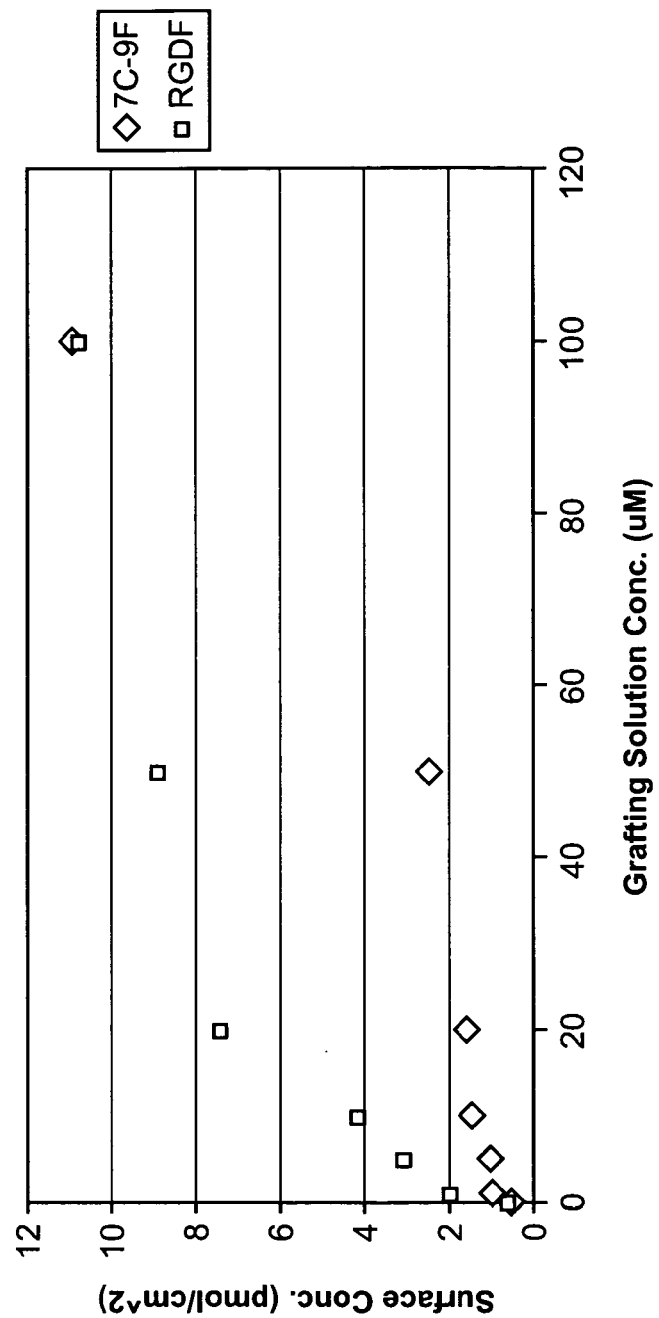
FIG. 11 depicts surface peptide concentration of fluorescent peptides on the interpenetrating network (IPN).

Peptides containing a FITC molecule were grafted onto IPN surfaces at various peptide concentrations. The amount of peptide bound to the surface was quantified by cleaving off the FITC tag with chymotrypsin and measuring the resulting fluorescence. The results are shown in FIG. 11. The 7C-9 peptide was found in the bacterial peptide display selections and is a novel peptide. The RGD peptide has been shown to allow for similar cell attachment and proliferation on the IPN surface in comparison to laminin-coated surfaces. The 7C-9 peptide attaches to the surface at lower concentrations in comparison to the RGD peptide though it can saturate the surface at high peptide grafting concentration.

Figure 12:
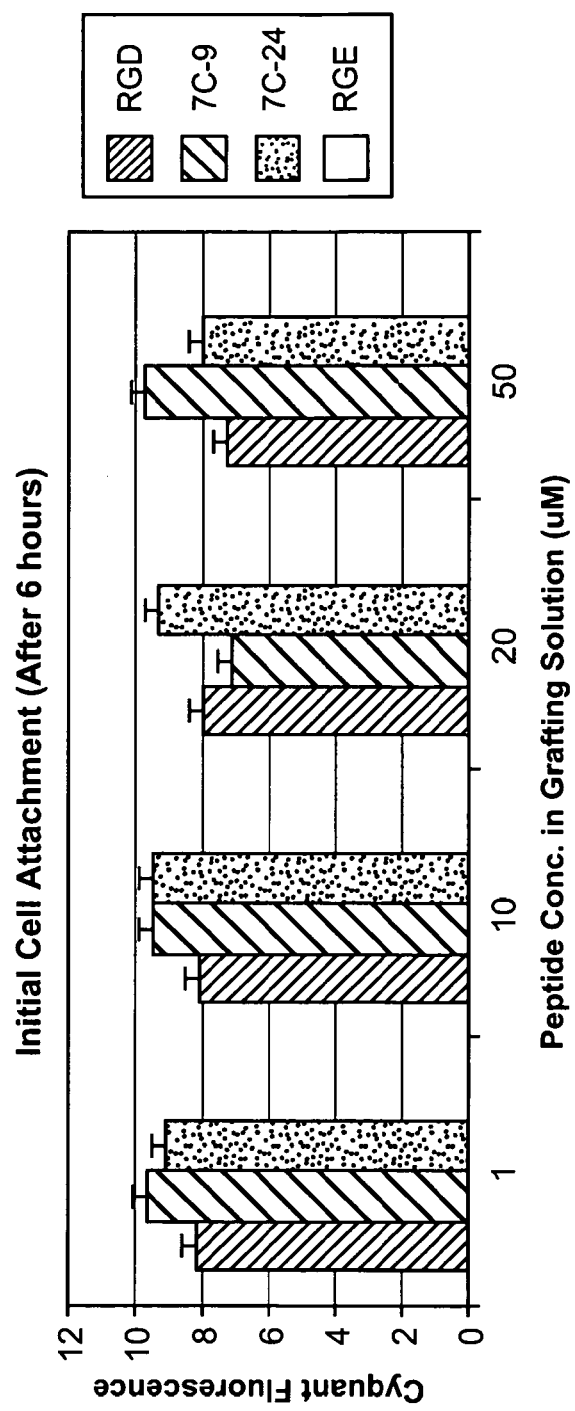
FIG. 12 depicts initial cell attachment on peptide-grafted IPNs.

IPNs were grafted with RGD, 7C-9, and 7C-24 peptides at various concentrations. After allowing neural stem cells attach to the surface for 6 hours, the amount of cells was quantified with Cyquant, a fluorescent DNA-binding dye. The data are shown in FIG. 12. The cell attachment was similar for all surfaces except for RGE where the amount of cells was below the detection limit of the assay. *=Below detection limit of the assay.

Figure 13:
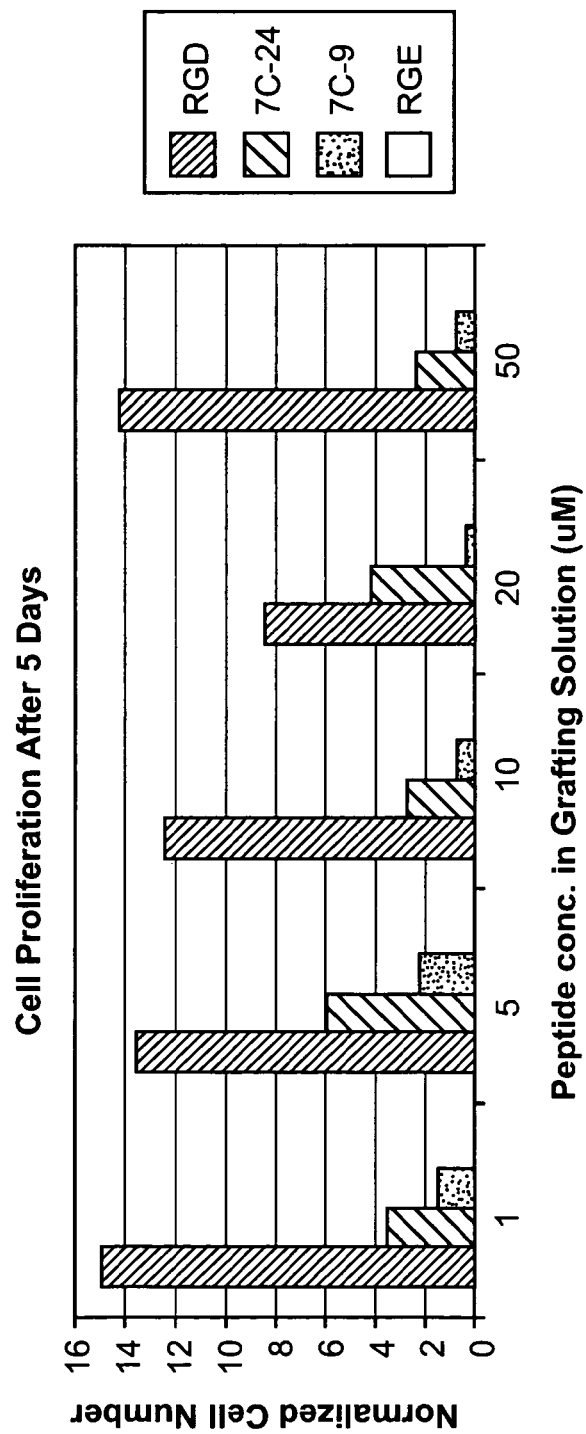
FIG. 13 depicts cell proliferation on peptide-grafted IPNs after 5 days.

Cell proliferation was quantified on peptide-grafted IPN surfaces after 5 days with Cyquant. The cell number was normalized to the amount of cells seeded on the IPN surfaces. The data are shown in FIG. 13. The RGD-grafted surfaces show a much higher amount of cell proliferation than 7C-9 and 7C-24-grafted surfaces though 7C-9 surfaces have a lower peptide surface concentration compared to the RGD surfaces. A control surface with an RGE peptide was shown to have little or no cells detached. *=Below the detection limit of the assay.

Figure 14:
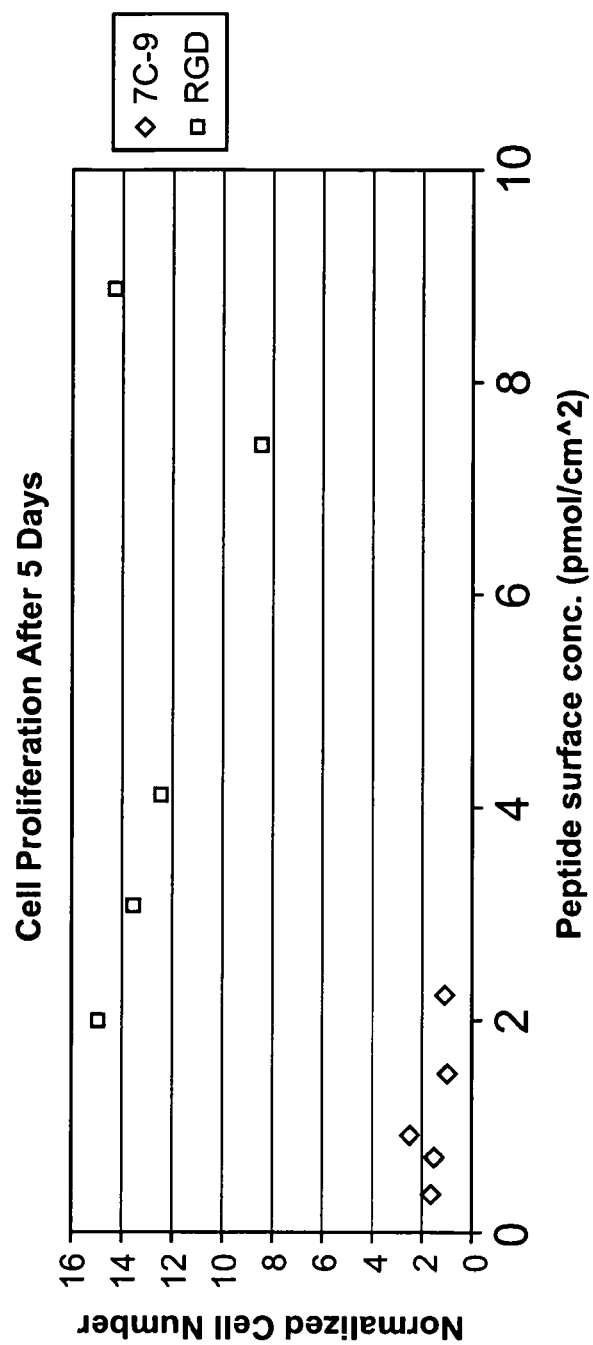
FIG. 14 depicts cell proliferation after 5 days based on surface peptide concentration.

Cell proliferation was quantified on peptide-grafted IPN surfaces after 5 days with Cyquant. The cell number was normalized to the amount of cells seeded on the IPN surfaces. The data are shown in FIG. 14. Comparing the 7C-9 peptide surfaces at low peptide surface concentrations with the RGD surfaces at similar peptide concentrations, it appears that there is slower proliferation on the 7C-9 surfaces.

Example 8

Biomaterial Screening Through Analysis of Stem Cell Function and Self-Renewal

For a smaller set of as many as 6 peptides that support attachment, the following comprehensive assays are conducted in vitro and in vivo to analyze hESC behavior on the hydrogels: 1) cell viability, 2) relative Akt signal activation, 3) cell proliferation, 4) SSEA-4 and Tra-1-80 self-renewal marker analysis, 5) Oct4 self-renewal marker analysis, 6) hTERT self-renewal marker analysis, 7) karyotype analysis, 8) embryoid body differentiation, and 9) teratoma formation. In addition, the following control surfaces are used: 1) tissue culture polystyrene with adsorbed gelatin (negative control for self-renewal, as in FIG. 7), 2) MEFs (positive control for self-renewal, as in FIG. 7), 3) Matrigel (positive control),[82] 4) sIPNs with no peptide (negative cell attachment control), 5) sIPNs with the bsp-RGE(15) peptide (negative cell attachment control, as in FIGS. 8), and 6) sIPNs with the bsp-RGD (15) peptide (benchmark control, as in FIG. 8).

Cell viability (assayed after 48 hours) is examined using the calcein-AM stain (Molecular Probes) and plotted as a function of peptide concentration. Steady state (48 hour) Akt activation is assayed by Western blotting (FIG. 8). Proliferation data (assayed after 96 hours) are collected using the CyQuant assay (FIG. 3) and likewise plotted as a function of peptide concentration.

More detailed, long-term biological analysis is conducted on as many as 6 hydrogel surfaces (i.e. peptides at a specific concentration) that yield the most robust viability, signaling, and proliferation responses. For these medium-term studies, the peptides are incorporated into the same IPN hydrogel demonstrated to have promise for hESC culture. hESC maintenance in an undifferentiated state after five cell passages on the surfaces is assessed via numerous standard approaches established in the literature 82, 87, 113. Morphology and cell/nucleus ratios are assessed qualitatively, as demonstrated in FIG. 7. Immunostaining is combined with flow cytometry to quantify the percentage of cells expressing key hESC markers.[82] Briefly, cells are dissociated using a 0.5 mM EDTA solution, blocked with rabbit serum, incubated in primary antibodies for SSEA-4 and Tra-1-80 (Chemicon), and incubated with the appropriate Alexa 488, Cy3, or Cy5-labeled secondary rabbit antibodies (Jackson ImmunoResearch). Cells are then analyzed via flow cytometry. Taqman QPCR is conducted essentially as above (FIG. 5, Preliminary Studies) using previously developed primers and probes to quantify hESC transcription factor expression (Oct4) and telomerase activity (hTERT: the catalytic subunit of telomerase).[82] To move towards fully defined systems, studies are conducted with H1 cells[17] (in NC-SFM medium) and are confirmed with HSF6 cells (in KSR medium).

Cells are also cultured on IPNs coated with bsp-RGD(15) in NC-SFM plus all chemically synthesized soluble peptides at 100 nM and 1 µM for five passages. If colonies morphologically consistent with hESC colonies are still present (FIG. 7), cells are subjected to SSEA-4 immunostaining and Oct4

QPCr. Note that Oct4+ hESCs could only be successfully expanded on bsp-RGD(15) for three passages.

For sIPNs that maintain hESC markers after five passages, a parallel experiment is conducted for 10 passages and self-renewal re-assessed as defined above. Matrices that support self-renewal at 10 passages are used to analyze chromosome stability and the ability of the cells to undergo differentiation. Specifically, cytogenetic analysis of 20-50 cells is performed using GTG-banding at the Medical Genetics Cytogenetics Laboratory (Children's Hospital, Oakland, Calif.), as previously described.[82] Furthermore, hESCs maintained in an immature state retain the ability to undergo differentiation into cells of the three germ layers. To assess the in vitro differentiation capacity of cultures, embryoid body differentiation analysis is conducted by collagenase dissociation of cultures after 10 passages into small clumps, followed by suspension in low attachment culture plates (Corning). Differentiation is conducted in 80% KO-DMEM, 20% FBS, and supplements as described [82]. After 4 days in suspension followed by 10 days on chamber slides, cells are processed and stained for ecotodermal (β-tubulin III staining for neurons, Sigma antibody), mesodermal (muscle actin staining, Dako Corp. antibody), and endodermal (α-fetoprotein, Sigma antibody) lineages. Finally, to assay the in vivo differentiation capabilities of hESCs expanded on synthetic surfaces, teratomas are formed via intramuscular injection of 5 million cells into the hindlimb of SCID/beige mice. After 75 days, tissue is analyzed by IDEXX for the presence of differentiated cells from the three germ layers (West Sacramento, Calif.), as described.[15, 17,19,82]

REFERENCES

1. Rezania, A. & Healy, K. E. Integrin subunits responsible for adhesion of human osteoblast-like cells to biomimetic peptide surfaces. *J Orthop Res* 17, 615-623 (1999).
2. Haugh, J. M., Codazzi, F., Teruel, M. & Meyer, T. Spatial sensing in fibroblasts mediated by 3' phosphoinositides. *J Cell Biol* 151, 1269-1280 (2000).
3. Harbers, G. M. & Healy, K. E. The Effect of Ligand Type and Density on Osteoblast Adhesion, Proliferation and Matrix Mineralization. *J. Biomed. Mater. Res* In Press (2005).
4. Harbers, G. M., Barber, T. A., Stile, R. A., Sumner, D. R. & Healy, K. E. in Biomimetic Materials and Design: Interactive Biointerfacial Strategies, Tissue Engineering and Drug Delivery. (eds. A. K. Dillow & A. Lowman) 55-90 (Marcel Dekker, New York; 2002).
5. Harbers, G. A., Gamble, L. J., Irwin, E. F., Castner, D. G. & Healy, K. E. Development and characterization of a high-throughput system for assessing cell-surface receptor-ligand engagement. *Langmuir* 21, 8374-8384 (2005).
6. Kunkel, M. T., Ni, Q., Tsien, R. Y., Zhang, J. & Newton, A. C. Spatio-temporal dynamics of protein kinase B/Akt signaling revealed by a genetically encoded fluorescent reporter. *J Biol Chem* 280, 5581-5587 (2005).
7. Emsley, J. G. & Hagg, T. alpha 6 beta 1 integrin directs migration of neuronal precursors in adult mouse forebrain. *Experimental Neurology* 183, 273-285 (2003).
8. Murayama, O., Nishida, H. & Sekiguchi, K. Novel peptide ligands for integrin alpha 6 beta 1 selected from a phage display library. *Journal of Biochemistry* 120, 445-451 (1996).
9. Ivaska, J. et al. A peptide inhibiting the collagen binding function of integrin alpha 1-2 domain. *J. Biol. Chem.* 274, 3513-3521 (1999).
10. Richards, M., Fong, C. Y., Chan, W. K., Wong, P. C. & Bongso, A. Human feeders support prolonged undifferentiated growth of human inner cell masses and embryonic stem cells. *Nat Biotechnol* 20, 933-936 (2002).
11. Richards, M. et al. Comparative evaluation of various human feeders for prolonged undifferentiated growth of human embryonic stem cells. *Stem Cells* 21, 546-556 (2003).
12. Hovatta, O. et al. A culture system using human foreskin fibroblasts as feeder cells allows production of human embryonic stem cells. *Hum Reprod* 18, 1404-1409 (2003).
13. Amit, M. et al. Human feeder layers for human embryonic stem cells. *Biol Reprod* 68, 2150-2156 (2003).
14. Gehlsen, K. R., Sriramarao, P., Furcht, L. T. & Skubitz, A. P. A synthetic peptide derived from the carboxy terminus of the laminin A chain represents a binding site for the alpha 3 beta 1 integrin. *J Cell Biol* 117, 449-459. (1992).
15. Ludwig, T. E. et al. Derivation of human embryonic stem cells in defined conditions. *Nat Biotechnol* (2006).
16. Martin, M. J., Muotri, A., Gage, F. & Varki, A. Human embryonic stem cells express an immunogenic nonhuman sialic acid. *Nat Med* 11, 228-232 (2005).
17. Thomson, J. A. et al. Embryonic stem cell lines derived from human blastocysts. *Science* 282, 1145-1147 (1998).
18. Reubinoff, B. E., Pera, M. F., Fong, C. Y., Trounson, A. & Bongso, A. Embryonic stem cell lines from human blastocysts: somatic differentiation in vitro. *Nat Biotechnol* 18, 399-404 (2000).
19. Xu, C. et al. Feeder-free growth of undifferentiated human embryonic stem cells. *Nat Biotechnol* 19, 971-974 (2001).
20. Cheng, L., Hammond, H., Ye, Z., Zhan, X. & Dravid, G. Human adult marrow cells support prolonged expansion of human embryonic stem cells in culture. *Stem Cells* 21, 131-142 (2003).
21. Semler, E. J., Ranucci, C. S. & Moghe, P. V. Mechanochemical manipulation of hepatocyte aggregation can selectively induce or repress liver-specific function. *Biotechnology and Bioengineering* 69, 359-369 (2000).
22. Albelda, S. M. & Buck, C. A. Integrins and other cell adhesion molecules. *The FASEB J.* 4, 2868-2880 (1990).
23. Ruoslahti, E. & Pierschbacher, M. D. Arg-Gly-Asp: A versitile cell recognition signal. *Cell* 44, 517-518 (1986).
24. Massia, S. P. & Hubbell, J. A. Immobilized amines and basic amino acids as mimetic heparin-binding domains for cell surface proteoglycan-mediated adhesion. *J. Biolog. Chem.* 267, 10133-10141 (1992).
25. Drumheller, P. D., Elbert, D. L. & Hubbell, J. A. Multifunctional poly(ethylene glycol) semi-interpenetrating polymer networks as highly selective adhesive substrates for bioadhesive peptide grafting. *Biotechnology and Bioengineering* 43, 772-780 (1994).
26. Massia, S. P. & Hubbell, J. A. Human endothelial cell interactions with surface-coupled adhesion peptides on a nonadhesive glass substrate and two polymeric biomaterials. *J. Biomed. Mater. Res.* 25, 223-242 (1991).
27. Drumheller, P. D., Elbert, D. L. & Hubbell, J. A. Multifunctional poly(ethylene glycol) semi-interpenetrating networks as highly selective adhesive substrates for bioadhesive peptide grafting. *Biotechnol. Bioeng.* 43, 772-780 (1994).
28. Hubbell, J. A., Massia, S. P. & Drumheller, P. D. Surface-grafted cell binding peptides in tissue engineering of the vascular graft. *Annals of the New York Academy of Sciences* 655, 253-258 (1992).
29. Bearinger, J. P., Castner, D. G., Golledge, S. L., Hubchak, S. & Healy, K. E. P(AAm-co-EG) interpenetrating polymer networks grafted to oxide surfaces: surface character- 29. ization, protein adsorption, and cell detachment studies. *Langmuir* 13, 5175-5183 (1997).
30. Bearinger, J. P., Castner, D. G. & Healy, K. E. Biomolecular modification of p(AAm-co-EG/AA) IPNs supports osteoblast adhesion and phenotypic expression. *Journal of Biomaterials Science, Polymer Edition* 9, 629-652 (1998).
31. Ghosh, K., Ren, X. D., Shu, X. Z., Prestwich, G. D. & Clark, R. A. Fibronectin functional domains coupled to hyaluronan stimulate adult human dermal fibroblast responses critical for wound healing. Tissue engineering 12, 601-613 (2006).
32. Rezania, A., Thomas, C. H., Branger, A. B., Waters, C. M. & Healy, K. E. The detachment strength and morphology of bone cells contacting materials modified with a peptide sequence found within bone sialoprotein. *J. Biomed. Mater. Res.* 37, 9-19 (1997).
33. Massia, S. P. & Hubbell, J. A. Covalent surface immobilization of Arg-Gly-Asp- and Tyr-Ile-Gly-Ser-Arg-containing peptides to obtain well-defined cell adhesive substrates. *Analytical Biochemistry* 187, 292-301 (1990).
34. Drumheller, P. D. & Hubbell, J. A. Polymer networks with grafted cell adhesion peptides for highly biospecific cell adhesive substrates. *Analytical Biochemistry* 222, 380-388 (1994).
35. Rowley, J. A., Madlambayan, G. & Mooney, D. J. Alginate hydrogels as synthetic extracellular matrix materials. *Biomaterials* 20, 45-53 (1999).
36. Moghaddam, M. J. & Matsuda, T. Molecular design of three-dimensional artificial extracellular matrix: photosensitive polymers containing cell adhesive peptide. *Journal of Polymer Science, Polymer Chemistry Edition* 31, 1589-1597 (1993).
37. Schense, J. C. & Hubbell, J. A. Three-dimensional migration of neurites is mediated by adhesion site density and affinity. *Journal of Biological Chemistry* 275, 6813-6818 (2000).
38. Alsberg, E., Anderson, K. W., Albeiruti, A., Franceschi, R. T. & Mooney, D. J. Cell-interactive alginate hydrogels for bone tissue engineering. *Journal of Dental Research* 80, 2025-2029 (2001).
39. Stile, R. A. & Healy, K. E. Peptide-modified thermoreversible hydrogels for tissue regeneration. Abstracts of Papers of the *American Chemical Society* 219, 584-POLY (2000).
40. Kim, S. & Healy, K. E. Synthesis and characterization of injectable poly(N-isopropylacrylamide-co-acrylic acid) hydrogels with proteolytically degradable cross-links. *Biomacromolecules* 4, 1214-1223 (2003).
41. Barber, T. A., Golledge, S. L., Castner, D. G. & Healy, K. E. Peptide-modified p(AAm-co-EG/AAc) IPNs grafted to bulk titanium modulate osteoblast behavior in vitro. *Journal of biomedical materials research* 64, 38-47 (2003).
42. Harbers, G. M., Barber, T. A., Yanez, M. E., Larman, H. B. & Healy, K. E. in Society for Biomaterials, Vol. 24 275St. Paul, Minn.; 2001).
43. Harbers, G. M., Barber, T. A., Yanez, M. E., Larman, H. B. & Healy, K. E. in AVS 48th International Symposium 221San Francisco, Calif.; 2001).
44. Li, Y. J., Chung, E. H., Rodriguez, R. T., Firpo, M. T. & Healy, K. E. Hydrogels as artificial matrices for human embryonic stem cell self-renewal. *Journal of biomedical materials research* 79, 1-5 (2006).
45. Engler, A. et al. Substrate Compliance versus Ligand Density in Cell on Gel Responses. *Biophysical Journal* 86, 617-628 (2004).
46. Engler, A. J. et al. Myotubes differentiate optimally on substrates with tissue-like stiffness: pathological implications for soft or stiff microenvironments. *J Cell Biol* 116, 877-887 (2004).
47. Lo, C. M., Wang, H. B., Dembo, M. & Wang, Y. L. Cell movement is guided by the rigidity of the substrate. Biophysical Journal 79, 144-152 (2000).
48. Kong, H. J., Polte, T. R., Alsberg, E. & Mooney, D. J. FRET measurements of cell-traction forces and nano-scale clustering of adhesion ligands varied by substrate stiffness. *Proc Natl Acad Sci USA* 102, 4300-4305 (2005).
49. Engler, A. J., Sen, S., Sweeney, H. L. & Discher, D. E. Matrix elasticity directs stem cell lineage specification. *Cell* 126, 677-689 (2006).
50. Peyton, S. R. & Putnam, A. J. Extracellular matrix rigidity governs smooth muscle cell motility in a biphasic fashion. *Journal of cellular physiology* 204, 198-209 (2005).
51. Chen, C. S., Mrksich, M., Huang, S., Whitesides, G. M. & Ingber, D. E. Geometric control of cell life and death. *Science* 276, 1425-1428 (1997).
52. Singhvi, R. et al. Engineering cell shape and function. *Science.* 264, 696-698 (1994).
53. Thomas, C. H., Collier, J. H., Sfeir, C. S. & Healy, K. E. Engineering gene expression and protein synthesis by modulation of nuclear shape. *Proceedings of the National Academy of Sciences of the United States of America* 99, 1972-1977 (2002).
54. McBeath, R., Pirone, D. M., Nelson, C. M., Bhadriraju, K. & Chen, C. S. Cell Shape, Cytoskeletal Tension, and RhoA Regulate Stem Cell Lineage Commitment. *Developmental Cell* 6, 483-495 (2004).
55. Thomas, C. H., Lhoest, J. B., Castner, D. G., McFarland, C. D. & Healy, K. E. Surfaces designed to control the projected area and shape of individual cells. *Journal of Biomechanical Engineering* 121, 40-48 (1999).
56. Maniotis, A. J., Chen, C. S. & Ingber, D. E. Demonstration of mechanical connections between integrins cytoskeletal filaments, and nucleoplasm that stabilize nuclear structure. *Proceedings of the National Academy of Sciences of the United States of America* 94, 849-854 (1997).
57. Easty, G. C., Easty, D. M. & Ambrose, E. J. Studies of cellular adhesiveness. *Expt. Cell. Res.* 19, 539-548 (1960).
58. Irwin, E. F., Ho, J. E., Kane, S. R. & Healy, K. E. Analysis of interpenetrating polymer networks via quartz crystal microbalance with dissipation monitoring. *Langmuir* 21, 5529-5536 (2005).
59. Arap, W., Pasqualini, R. & Ruoslahti, E. Cancer treatment by targeted drug delivery to tumor vasculature in a mouse model. *Science* 279, 377-380 (1998).
60. Kolonin, M. G. et al. Ligand-directed surface profiling of human cancer cells with combinatorial Peptide libraries. *Cancer Res* 66, 34-40 (2006).
61. Smith, G. P. Filamentous fusion phage: novel expression vectors that display cloned antigens on the virion surface. *Science* 228, 1315-1317 (1985).
62. Landon, L. A. & Deutscher, S. L. Combinatorial discovery of tumor targeting peptides using phage display. *J Cell Biochem* 90, 509-517 (2003).
63. Dane, K. Y., Chan, L. A., Rice, J. J. & Daugherty, P. S. Isolation of cell specific peptide ligands using fluorescent bacterial display libraries. *J Immunol Methods* 309, 120-129 (2006).
64. Harbers, G. M. & Healy, K. E. The effect of ligand type and density on osteoblast adhesion, proliferation, and matrix mineralization. *Journal of biomedical materials research* (2005).

65. Agrawal, S. & Schaffer, D. V. In situ stem cell therapy: novel targets, familiar challenges. *Trends Biotechnol* 23, 78-83 (2005).
66. O'Neill, A. & Schaffer, D. V. The biology and engineering of stem cell control. *Biotechnology and applied biochemistry* (2004).
67. Lai, K., Kaspar, B. K., Gage, F. H. & Schaffer, D. V. Sonic hedgehog regulates adult neural progenitor proliferation in vitro and in vivo. *Nat Neurosci* 6, 21-27. (2003).
68. Abranches, E., O'Neill, A., Robertson, M. J., Schaffer, D. V. & Cabral, J. M. Development of quantitative PCR methods to analyse neural progenitor cell culture state. *Biotechnology and applied biochemistry* 44, 1-8 (2006).
69. Palmer, T. D., Takahashi, J. & Gage, F. H. The adult rat hippocampus contains primordial neural stem cells. *Mol Cell Neurosci* 8, 389-404 (1997).
70. Tai, Y. T. & Svendsen, C. N. Stem cells as a potential treatment of neurological disorders. *Curr Opin Pharmacol* 4, 98-104 (2004).
71. Tashiro, K. et al. The RGD containing site of the mouse laminin A chain is active for cell attachment, spreading, migration and neurite outgrowth. *Journal of cellular physiology* 146, 451-459 (1991).
72. Sen, A., Kallos, M. S. & Behie, L. A. Passaging protocols for mammalian neural stem cells in suspension bioreactors. *Biotechnol Prog.* 18, 337-345 (2002).
73. Lendahl, U., Zimmerman, L. B. & McKay, R. D. CNS stem cells express a new class of intermediate filament protein. *Cell* 60, 585-595. (1990).
74. Ranieri, J. P. et al. Neuronal cell attachment to fluorinated ethylene propylene films with covalently immobilized laminin oligopeptides YIGSR and IKVAV. II. *Journal of Biomedical Materials Research* 29, 779-785 (1995).
75. Saneinejad, S. & Shoichet, M. S. Patterned glass surfaces direct cell adhesion and process outgrowth of primary neurons of the central nervous system. *Journal of Biomedical Materials Research* 42, 13-19 (1998).
76. Silva, G. A. et al. Selective differentiation of neural progenitor cells by high-epitope density nanofibers. *Science* 303, 1352-1355 (2004).
77. Rice, J. J., Schohn, A., Bessette, P. H., Boulware, K. T. & Daugherty, P. S. Bacterial display using circularly permuted outer membrane protein X yields high affinity peptide ligands. *Protein Sci* (in press).
78. Bessette, P. H. & Daugherty, P. S. Flow cytometric screening of cDNA expression libraries for fluorescent proteins. *Biotechnol Prog* 20, 963-967 (2004).
79. Dane, K. Y., Chan, L. A., Rice, J. J. & Daugherty, P. S. Isolation of cell specific peptide ligands using fluorescent bacterial display libraries. *J Immunol Methods* (in press).
80. Bodnar, M. S., Meneses, J. J., Rodriguez, R. T. & Firpo, M. T. Propagation and maintenance of undifferentiated human embryonic stem cells. *Stem Cells Dev* 13, 243-253 (2004).
81. Abeyta, M. J. et al. Unique gene expression signatures of independently-derived human embryonic stem cell lines. *Hum Mol Genet.* 13, 601-608 (2004).
82. Li, Y., Powell, S., Brunette, E., Lebkowski, J. & Mandalam, R. Expansion of human embryonic stem cells in defined serum-free medium devoid of animal-derived products. *Biotechnol Bioeng* 91, 688-698 (2005).
83. Brandenberger, R. et al. Transcriptome characterization elucidates signaling networks that control human ES cell growth and differentiation. *Nat Biotechnol* 22, 707-716 (2004).
84. Miura, T. et al. Monitoring early differentiation events in human embryonic stem cells by massively parallel signature sequencing and expressed sequence tag scan. *Stem Cells Dev* 13, 694-715 (2004).
85. Brandenberger, R. et al. MPSS profiling of human embryonic stem cells. *BMC Dev Biol* 4, 10 (2004).
86. Wei, C. L. et al. Transcriptome profiling of human and murine ESCs identifies divergent paths required to maintain the stem cell state. *Stem Cells* 23, 166-185 (2005).
87. Xu, C. H. et al. Feeder-free growth of undifferentiated human embryonic stem cells. *Nature Biotechnology* 19, 971-974 (2001).
88. Miner, J. H. & Yurchenco, P. D. Laminin functions in tissue morphogenesis. *Annu Rev Cell Dev Biol* 20, 255-284 (2004).
89. Giancotti, F. G. & Tarone, G. Positional control of cell fate through joint integrin/receptor protein kinase signaling. *Annu Rev Cell Dev Biol* 19, 173-206 (2003).
90. Downward, J. PI 3-kinase, Akt and cell survival. *Semin Cell Dev Biol* 15, 177-182 (2004).
91. Luo, J., Manning, B. D. & Cantley, L. C. Targeting the PI 3K-Akt pathway in human cancer: rationale and promise. *Cancer Cell* 4, 257-262 (2003).
92. Mora, A., Komander, D., van Aalten, D. M. & Alessi, D. R. PDK1, the master regulator of AGC kinase signal transduction. *Semin Cell Dev Biol* 15, 161-170 (2004).
93. Harris, T. E. & Lawrence, J. C., Jr. TOR signaling. *Sci STKE* 2003, rel 5 (2003).
94. Kim, S. J. et al. Contribution of the PI3K/Akt/PKB signal pathway to maintenance of self-renewal in human embryonic stem cells. *FEBS Lett* 579, 534-540 (2005).
95. Paling, N. R., Wheadon, H., Bone, H. K. & Welham, M. J. Regulation of embryonic stem cell self-renewal by phosphoinositide 3-kinase-dependent signaling. *J Biol Chem* 279, 48063-48070 (2004).
96. Becker, S., Schmoldt, H. U., Adams, T. M., Wilhelm, S. & Kolmar, H. Ultra-high-throughput screening based on cell-surface display and fluorescence-activated cell sorting for the identification of novel biocatalysts. *Curr Opin Biotechnol* 15, 323-329 (2004).
97. Nguyen, A. W. & Daugherty, P. S. Evolutionary optimization of fluorescent proteins for intracellular FRET. *Nat Biotechnol* 23, 355-360 (2005).
98. Shaner, N. C., Steinbach, P. A. & Tsien, R. Y. A guide to choosing fluorescent proteins. *Nat Methods* 2, 905-909 (2005).
99. Weinberger, L. S., Burnett, J. C., Toettcher, J. E., Arkin, A. P. & Schaffer, D. V. Stochastic gene expression in a lentiviral positive-feedback loop: HIV-1 Tat fluctuations drive phenotypic diversity. *Cell* 122, 169-182 (2005).
100. Yu, J. H. & Schaffer, D. V. Selection of novel vesicular stomatitis virus glycoprotein variants from a peptide insertion library for enhanced purification of retroviral and lentiviral vectors. *Journal of virology* 80, 3285-3292 (2006).
101. Gropp, M. et al. Stable genetic modification of human embryonic stem cells by lentiviral vectors. *Mol Ther* 7, 281-287 (2003).
102. Ma, Y., Ramezani, A., Lewis, R., Hawley, R. G. & Thomson, J. A. High-level sustained transgene expression in human embryonic stem cells using lentiviral vectors. *Stem Cells* 21, 111-117 (2003).
103. Kumar, A., Zhang, J. & Yu, F. S. Toll-like receptor 2-mediated expression of beta-defensin-2 in human corneal epithelial cells. *Microbes Infect* (2005).
104. Patel, T. R. & Corbett, S. A. Simvastatin suppresses LPS-induced Akt phosphorylation in the human monocyte cell line THP-1. *J Surg Res* 116, 116-120 (2004).
105. Guha, M. & Mackman, N. The phosphatidylinositol 3-kinase-Akt pathway limits lipopolysaccharide activation 106. Monje, M. L., Toda, H. & Palmer, T. D. Inflammatory blockade restores adult hippocampal neurogenesis. *Science* 302, 1760-1765 (2003).
107. Hem, D. L. & Hubbell, J. A. Incorporation of adhesion peptides into nonadhesive hydrogels useful for tissue resurfacing. *Journal of Biomedical Materials Research* 39, 266-276 (1998).
108. Koo, L. Y., Irvine, D. J., Mayes, A. M., Lauffenburger, D. A. & Griffith, L. G. Co-regulation of cell adhesion by nanoscale RGD organization and mechanical stimulus. *J Cell Sci* 115, 1423-1433. (2002).
109. Garcia, A. J., Huber, F. & Boettiger, D. Force required to break alpha5beta1 integrin-fibronectin bonds in intact adherent cells is sensitive to integrin activation state. *J. Biol. Chem.* 273, 10988-10993 (1998).
110. Asthagiri, A. R., Nelson, C. M., Horwitz, A. F. & Lauffenburger, D. A. Quantitative relationship among Integrin-ligand binding, adhesion, and signaling via focal adhesion kinase and extracellular signal-regulated kinase 2. *J. of Biological Chemistry* 274, 27119-27127 (1999).
111. Lotz, M. M., Burdsal, C. A., Erickson, H. P. & McClay, D. R. Cell adhesion to fibronectin and tenascin: quantitative measurements of initial binding and subsequent strengthening response. *J. Cell Biol.* 109, 1795-1805 (1989).
112. Weetall, M. et al. A homogeneous fluorometric assay for measuring cell adhesion to immobilized ligand using V-well microtiter plates. *Anal Biochem* 293, 277-287 (2001).
113. Xu, C. H. et al. Basic fibroblast growth factor supports undifferentiated human embryonic stem cell growth without conditioned medium. *Stem Cells* 23, 315-323 (2005).
114. Harbers, G. M., Gamble, L. J., Irwin, E. F., Castner, D. G. & Healy, K. E. Development and characterization of a high-throughput system for assessing cell-surface receptor-ligand engagement. *Langmuir* 21, 8374-8384 (2005).
115. Abranches, E., O'Neill, A., Robertson, M. J., Schaffer, D. V. & Cabral, J. Development of Quantitative PCR Methods to Analyze Adult Neural Progenitor Cell Culture State. *Biotechnol. & Appl. Biochem.* (in press).
116. Lai, K., Robertson, M. J. & Schaffer, D. V. The sonic hedgehog signaling system as a bistable genetic switch. *Biophys J* 86, 2748-2757 (2004).
117. Saha, K. & Schaffer, D. V. Signal dynamics in Sonic hedgehog tissue patterning. *Development* 133, 889-900 (2006).
118. Lauffenburger, D. A. & Schaffer, D. V. The matrix delivers. *Nat Med* 5, 733-734 (1999).
119. Schaffer, D. V. & Lauffenburger, D. A. Optimization of cell surface binding enhances efficiency and specificity of molecular conjugate gene delivery. *J Biol Chem* 273, 28004-28009 (1998).
120. Schaffer, D. V., Fidelman, N. A., Dan, N. & Lauffenburger, D. A. Vector unpacking as a potential barrier for receptor-mediated polyplex gene delivery. *Biotechnol Bioeng* 67, 598-606 (2000).
121. Schaffer, D. V. & Lauffenburger, D. A. Targeted synthetic gene delivery vectors. *Curr. Opin. Mol. Ther.* 2, 155-161 (2000).
122. Kaspar, B. K. et al. Targeted retrograde gene delivery for neuronal protection. *Mol Ther* 5, 50-56 (2002).
123. Kaspar, B. K. et al. Adeno-associated virus effectively mediates conditional gene modification in the brain. *Proc Natl Acad Sci USA* 99, 2320-2325 (2002).
124. Wiewrodt, R. et al. Size-dependent intracellular immunotargeting of therapeutic cargoes into endothelial cells. *Blood* 99, 912-922. (2002).
125. Schaffer, D. V., Neve, R. L. & Lauffenburger, D. A. Use of the green fluorescent protein as a quantitative reporter of epidermal growth factor receptor-mediated gene delivery. *Tissue Engineering* 3, 53-63 (1997).
126. Maheshri, N., Koerber, J. T., Kaspar, B. K. & Schaffer, D. V. Directed evolution of adeno-associated virus yields enhanced gene delivery vectors. *Nat Biotechnol* 24, 198-204 (2006).
127. Yu, J. H. & Schaffer, D. V. High-throughput, library-based selection of a murine leukemia virus variant to infect nondividing cells. *Journal of virology* 80, 8981-8988 (2006).
128. Healy, K. E., Tsai, D. & Kim, J. E. Osteogenic cell attachment to degradable polymers. *Mat. res. Soc. Symp. Proc.* 252, 109-114 (1992).
129. Hockberger, P. E., Lom, B., Soekarno, A., Thomas, C. H. & Healy, K. E. in Nanofabrication and Biosystems: Integrating Material Science, Engineering and Biology. (eds. H. Hoch, L. Jelinski & H. Craighead) (In Press, 1996).
130. Bearinger, J. P. et al. P(AAm-co-EG) interpenetrating polymer networks grafted to oxide surfaces: Surface characterization, protein adsorption, and cell detachment studies. *Langmuir* 13, 5175-5183 (1997).
131. Healy, K. E., Rezania, A. & Stile, R. A. in Bioartificial Organs II: Technology, Medicine, and Materials, Vol. 875 24-35 1999).
132. Whang, K. et al. Engineering bone regeneration with bioabsorbable scaffolds with novel microarchitecture. *Tissue Engineering* 5, 35-51 (1999).
133. Stile, R. A. & Healy, K. E. Poly(N-isopropylacrylamide)-based semi-interpenetrating polymer networks for tissue engineering applications. 1. Effects of linear poly (acrylic acid) chains on phase behavior. *Biomacromolecules* 3, 591-600 (2002).
134. Barber, T. A., Golledge, S. L., Castner, D. G. & Healy, K. E. Peptide-modified p(AAm-co-EG/AAc) IPNs grafted to bulk titanium modulate osteoblast behavior in vitro. *Journal of Biomedical Materials Research Part A* 64A, 38-47 (2003).
135. Barber, T. A., Harbers, G. M., Park, S., Gilbert, M. & Healy, K. E. Ligand density characterization of peptide-modified biomaterials. *Biomaterials* 26, 6897-6905 (2005).
136. Saha, K., Schaffer, D. V. & Healy, K. E. Controlling neural stem cell behavior via peptide-modified hydrogels. *Abstracts Of Papers Of The American Chemical Society* 229, U200-U200 (2005).
137. Bessette, P. H., Rice, J. J. & Daugherty, P. S. Rapid isolation of high-affinity protein binding peptides using bacterial display. *Protein Eng Des Sel* 17, 731-739 (2004).
138. Daugherty, P. S., Iverson, B. L. & Georgiou, G. Flow cytometric screening of cell-based libraries. *J Immunol Methods* 243, 211-227 (2000).
139. Daugherty, P. S., Chen, G., Iverson, B. L. & Georgiou, G. Quantitative analysis of the effect of the mutation frequency on the affinity maturation of single chain Fv antibodies. *Proc Natl Acad Sci USA* 97, 2029-2034 (2000).
140. Daugherty, P. S., Olsen, M. J., Iverson, B. L. & Georgiou, G. Development of an optimized expression system for the screening of antibody libraries displayed on the *Escherichia coli* surface. *Protein Eng* 12, 613-621 (1999).
141. Daugherty, P. S., Chen, G., Olsen, M. J., Iverson, B. L. & Georgiou, G. Antibody affinity maturation using bacterial surface display. *Protein Eng* 11, 825-832 (1998).

142. Georgiou, G. et al. Display of heterologous proteins on the surface of microorganisms: from the screening of combinatorial libraries to live recombinant vaccines. *Nat Biotechnol* 15, 29-34 (1997).
143. Mena, M. A. & Daugherty, P. S. Automated design of degenerate codon libraries. *Protein Eng Des Sel* 18, 559-561 (2005).
144. Nguyen, A. W. & Daugherty, P. S. Production of randomly mutated plasmid libraries using mutator strains. *Methods Mol Biol* 231, 39-44 (2003).
145. Bessette, P. H., Mena, M. A., Nguyen, A. W. & Daugherty, P. S. Construction of designed protein libraries using gene assembly mutagenesis. *Methods Mol Biol* 231, 29-37 (2003).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A synthetic cell platform comprising:
   a) a synthetic substrate; and
   b) a mammalian stem cell-binding peptide covalently linked to the synthetic substrate, wherein the stem cell binding peptide has a length of up to about 50 amino acids, and wherein the stem cell binding peptide comprises the amino acid sequence SEQ ID NO: 22.

2. The synthetic cell platform of claim 1, wherein the stem cell-binding peptide is covalently linked to the synthetic substrate at a density of from about 0.1 pmol/cm$^2$ to about 100 pmol/cm$^2$.

3. The synthetic cell platform of claim 1, wherein the stem cell-binding peptide is covalently linked to the synthetic substrate at a density of from about 1 pmol/cm$^2$ to about 25 pmol/cm$^2$.

4. The synthetic cell platform of claim 1, wherein the synthetic substrate is an interpenetrating polymer network, a synthetic hydrogel, a semi-interpenetrating polymer network, or a thermo-responsive polymer.

5. The synthetic cell platform of claim 1, wherein the synthetic substrate comprises a co-polymer of polyacrylamide and poly(ethylene glycol).

6. The synthetic cell platform of claim 1, wherein the stem cell is an embryonic stem cell, a neural stem cell, a hematopoietic stem cell, a mesenchymal stem cell, or an induced pluripotent stem cell.

7. The synthetic cell platform of claim 1, further comprising a mammalian stem cell bound to the peptide.

* * * * *